US011877937B2

(12) United States Patent
Greenspan et al.

(10) Patent No.: US 11,877,937 B2
(45) Date of Patent: Jan. 23, 2024

(54) SPRINGS WITH STRAIN FEEDBACK

(71) Applicant: Accenture Global Solutions Limited, Dublin (IE)

(72) Inventors: Mark Benjamin Greenspan, San Francisco, CA (US); Lavinia Andreea Danielescu, San Francisco, CA (US)

(73) Assignee: Accenture Global Solutions Limited, Dublin (IE)

( * ) Notice: Subject to any disclaimer, the term of this patent is extended or adjusted under 35 U.S.C. 154(b) by 350 days.

(21) Appl. No.: 17/239,127

(22) Filed: Apr. 23, 2021

(65) Prior Publication Data

US 2022/0120325 A1 Apr. 21, 2022

Related U.S. Application Data

(60) Provisional application No. 63/092,688, filed on Oct. 16, 2020.

(51) Int. Cl.
*A61F 2/68* (2006.01)
*A61F 2/50* (2006.01)
*A61F 2/58* (2006.01)
*A61F 2/70* (2006.01)
*F16F 1/36* (2006.01)
*G01B 7/16* (2006.01)

(52) U.S. Cl.
CPC .............. *A61F 2/68* (2013.01); *A61F 2/5044* (2013.01); *A61F 2/583* (2013.01); *A61F 2/70* (2013.01); *F16F 1/3605* (2013.01); *G01B 7/18* (2013.01); *A61F 2002/5075* (2013.01); *A61F 2002/6827* (2013.01); *F16F 2226/04* (2013.01)

(58) Field of Classification Search
None
See application file for complete search history.

(56) References Cited

U.S. PATENT DOCUMENTS 3,603,142 A 9/1971 Saylak et al.
6,727,491 B1 * 4/2004 Dultz ............... G01B 11/18
385/12

(Continued)

FOREIGN PATENT DOCUMENTS

EP 3254925 12/2017
GB 2421075 A * 6/2006 ........... G01B 11/165

(Continued)

OTHER PUBLICATIONS

EP Partial Search Report in European Appln. No. 21195471.4, dated Mar. 22, 2022, 13 pages.

(Continued)

*Primary Examiner* — Melanie Torres Williams
(74) *Attorney, Agent, or Firm* — Fish & Richardson P.C.

(57) ABSTRACT

Springs can provide energy return and have a conductivity that changes in relation to an amount of strain or deformation of the spring. In some embodiments, the springs are made by multi-material 3D printing (additive manufacturing). Such springs made by multi-material 3D printing may include a first material that is electrically non-conductive and a second material that electrically conductive. The extent of deformation or strain of the spring may be determined or estimated by measuring the conductivity or resistivity of the electrically conductive material portion of the spring.

19 Claims, 12 Drawing Sheets

(56) References Cited

U.S. PATENT DOCUMENTS

| | | | |
|---|---|---|---|
| 9,352,629 B2 | 5/2016 | Chabanon et al. | |
| 2014/0283922 A1* | 9/2014 | Strom | B22F 10/28 267/180 |
| 2018/0122768 A1* | 5/2018 | Dugal | H01L 25/11 |
| 2020/0049648 A1 | 2/2020 | Kunc et al. | |

FOREIGN PATENT DOCUMENTS

| | | |
|---|---|---|
| WO | WO 2006/083913 | 8/2006 |
| WO | WO 2018/204565 | 11/2018 |
| WO | WO 2020/102527 | 5/2020 |

OTHER PUBLICATIONS

EP Extended Search Report in European Appln. No. 21195471.4, dated Jun. 23, 2022, 11 pages.
Adafruit.com [online], "USB LiIon/LiPoly charger—v1.2," available on or before Apr. 4, 2013 via Internet Archive: Wayback Machine URL<https://web.archive.org/web/20130404115906/https://www.adafruit.com/product/259>, retrieved on Sep. 3, 2021, retrieved from URL<https://www.adafruit.com/product/259>, 7 pages.
Adidas.com [online], "4DFWD," available on or before Dec. 9, 2018 via Internet Archive: Wayback Machine URL<https://web.archive.org/web/20181209101026/https://www.adidas.com/us/4D>, retrieved on Sep. 3, 2021, retrieved from URL<https://www.adidas.com/us/4D>, 2 pages.
American Orthotic & Prosthetic Association, "O&P Almanac: Apr. 2016," Apr. 4, 2016, retrieved on Sep. 7, 2021, retrieved from URL<https://issuu.com/americanoandp/docs/april_2016_almanac>, 39 pages.
Autodesk.com [online], "Fusion 360," available on or before Jun. 29, 2013 via Internet Archive: Wayback Machine URL<https://web.archive.org/web/20130629013046/https://www.autodesk.com/products/fusion-360/overview>, retrieved on Sep. 3, 2021, retrieved from URL<https://www.autodesk.com/products/fusion-360/overview>, 6 pages.
Bandyopadhyay et al., "Additive manufacturing of multi-material structures," Mater. Sci. Eng. R Reports, Jul. 2018, 129:1-16.
Blank et al., "Identifying the Role of Proprioception in Upper-Limb Prosthesis Control: Studies on Targeted Motion," ACM Transactions on Applied Perception, Jun. 2010, 7(3):15, 23 pages.
Blickhan, "The Spring-mass Model for Running and Hopping," J. Biomechanics, 1989, 22(11-12):1217-1227.
BYU.edu [online], "Compliant Mechanisms Explained," available on or before Feb. 9, 2019 via Internet Archive: Wayback Machine URL<https://web.archive.org/web/20190209124255/https://www.compliantmechanisms.byu.edu/about-compliant-mechanisms>, retrieved on Sep. 3, 2021, retrieved from URL<https://www.compliantmechanisms.byu.edu/about-compliant-mechanisms>, 8 pages.
Carbon3D.com [online], "Rethinking foam—the Carbon lattice innovation," available on or before Sep. 26, 2020 via Internet Archive: Wayback Machine URL<https://web.archive.org/web/20200926042305/https://www.carbon3d.com/resources/whitepaper/rethinking-foam-carbons-lattice-innovation/>, retrieved on Sep. 3, 2021, retrieved from URL<https://www.carbon3d.com/resources/whitepaper/rethinking-foam-carbons-lattice-innovation/>, 11 pages.
Chuckit-toys.co.uk [online], "Chuckit! Sport Launcher," available on or before Apr. 28, 2016 via Internet Archive: Wayback Machine URL<https://web.archive.org/web/20160428080237/https://www.chuckit-toys.co.uk/our-products/launchers/chuckit-sport-launcher.html>, retrieved on Sep. 3, 2021, retrieved from URL<https://www.chuckit-toys.co.uk/our-products/launchers/chuckit-sport-launcher.html>, 2 pages.
EnablingTheFuture.com [online], "Enabling The Future," available on or before Feb. 28, 2014 via Internet Archive: Wayback Machine URL<https://web.archive.org/web/20140228201637/http://enablingthefuture.org/>, retrieved on Sep. 3, 2021, retrieved from URL<http://enablingthefuture.org/>, 7 pages.

Engadget.com [online], "Haptic feedback gives prosthetics 'muscle sense'," May 30, 2017, retrieved on Sep. 3, 2021, retrieved from URL<https://www.engadget.com/2017-05-30-haptic-feedback-gives-prosthetics-muscle-sense.html?guccounter=1&guce_referrer=aHR0cHM6Ly93d3cuZ29vZ2xlLmNvbS8&guce_referrer_sig=AQAAAGrzAbBDwDyl3TDp3RcPkh6rLUpaliA6sCUFBoPnD_IaWLNna-0dnMOiCM-tkL_C8DqjglsP3lasYnCykzQMYZQ42nChyMNBqNHSWlQjpiGXQSotwyxxIZzWMMuM8B5rf8zM7Z2k9Qzkdm5WWyPIL6uvPLB3zrJkTo2nwedKSFBe>, 4 pages.
Farserotu et al., "Tactile Prosthetics in WiseSkin," Presented at Proceedings of the 2015 Design, Automation & Test in Europe Conference & Exhibition, Grenoble, France, Mar. 9-13, 2015, 1695-1697.
Formlabs.com [online], "Guide to Stereolithography (SLA) 3D Printing," available on or before Apr. 26, 2017 via Internet Archive: Wayback Machine URL<https://web.archive.org/web/20170426223030/https://formlabs.com/blog/ultimate-guide-to- stereolithography-sla-3d-printing/>, retrieved on Sep. 3, 2021, retrieved from URL<https://formlabs.com/blog/ultimate-guide-to-stereolithography-sla-3d-printing/>, 30 pages.
Greenspan et al., "Designing Low-Cost Sports Prosthetics with Advanced 3D Printing Techniques," Presented at Proceedings of UIST '20 Adjunct: Adjunct Publication of the 33rd Annual ACM Symposium on User Interface Software and Technology, Oct. 20, 2020, 126-128.
He et al., "Ondulé: Designing and Controlling 3D Printable Springs," Presented at Proceedings of the 32nd Annual ACM Symposium on User Interface Software and Technology, New Orleans, LA, USA, Oct. 20-23, 2019, 739-750.
Humphreys et al., "The Size and Scope of the Sports Industry in the United States: Estimates of the Size of the Sports Industry in the United States," Presented at Proceedings of the 10th Annual IASE Conference, Gijón, Spain, May 2008, 40 pages.
Hung et al., "Finger and Palm Dynamic Pressure Monitoring for Basketball Shooting," J. Sensors, May 2017, 2017(2):1-5.
Matthews et al., "Return to sport following an amputation," J. Sports Med. Phys. Fitness, Aug. 2014, 54(4):481-486.
Nemah et al., "A Review of Non-Invasive Haptic Feedback stimulation Techniques for Upper Extremity Prostheses," Int. J. Integr. Engineering, Apr. 2019, 11(1):299-326.
Okubo et al., "Kinematics of Arm Joint Motions in Basketball Shooting," Procedia Engineering, 2015, 112:443-448.
Ossur.com [online], "Flex-Foot Cheetah," available on or before Nov. 11, 2020 via Internet Archive: Wayback Machine URL<https://web.archive.org/web/20201111162754/https://www.ossur.com/en-us/prosthetics/feet/flex-foot-cheetah>, retrieved on Sep. 7, 2021, retrieved from URL<https://www.ossur.com/en-us/prosthetics/feet/flex-foot-cheetah>, 7 pages.
OT4-Orthopaedietechnik.com [online], "Products," available on or before Mar. 24, 2019 via Internet Archive: Wayback Machine URL<https://web.archive.org/web/20190324064459/https://www.ot4-orthopaedietechnik.com/Produkte>, retrieved on Sep. 7, 2021, retrieved from URL<https://www.ot4-orthopaedietechnik.com/produkte>, 2 pages (with English translation).
Pinshape.com [online], ""Spock" Basketball Prosthetic Hand," available on or before Mar. 7, 2021 via Internet Archive: Wayback Machine URL<https://web.archive.org/web/20210307051825/https://pinshape.com/items/24569-3d-printed-spock-basketball-prosthetic-hand>, retrieved on Sep. 3, 2021, retrieved from URL<https://pinshape.com/items/24569-3d-printed-spock-basketball-prosthetic-hand>, 9 pages.
Proto-pasta.com [online], "Electrically Conductive Composite PLA," available on or before May 7, 2015 via Internet Archive: Wayback Machine URL<https://web.archive.org/web/20150507001513/https://www.proto-pasta.com/products/conductive-pla>, retrieved on Sep. 7, 2021, retrieved from URL<https://www.proto-pasta.com/products/conductive-pla>, 5 pages.
Psyonic.io [online], "The Ability Hand," upon information and belief, available no later than Oct. 16, 2020, retrieved on Sep. 7, 2021, retrieved from URL<https://www.psyonic.io/ability-hand>, 8 pages.
Schmidt et al., "3D-printed prosthetics for the developing world," Presented at Proceedings of SIGGRAPH '15: Special Interest

(56) References Cited

OTHER PUBLICATIONS

Group on Computer Graphics and Interactive Techniques Conference, Los Angeles, CA, USA, Aug. 9-13, 2015, Article No. 21, 1 page.

Skylar-Scott et al., "Voxelated soft matter via multimaterial multinozzle 3D printing," Nature, Nov. 13, 2019, 575(7783):330-335.

Struzik et al., "Biomechanical Analysis of the Jump Shot in Basketball," J. Hum. Kinetics, Sep. 29, 2014, 42:73-79.

Tong et al., "Low-cost sensor-integrated 3D-printed personalized prosthetic hands for children with amniotic band syndrome: A case study in sensing pressure distribution on an anatomical human-machine interface (AHMI) using 3D-printed conformal electrode arrays," PLoS One, Mar. 28, 2019, 14(3):e0214120, 23 pages.

TRSProsthetics.com [online], "Hoopster," available on or before Apr. 19, 2016 via Internet Archive: Wayback Machine URL<https://web.archive.org/web/20160419155343/https://www.trsprosthetics.com/product/basketball-hoopster/>, retrieved on Sep. 7, 2021, retrieved from URL<https://www.trsprosthetics.com/product/basketball-hoopster/>, 2 pages.

Ultimaker, "Technical data sheet PLA," Version 4.002, dated Nov. 19, 2018, 3 pages.

Ultimaker, "Technical data sheet TPU 95A," Version 3.010, dated May 16, 2017, 3 pages.

Ultimaker.com [online], "Ultimaker Cura," available on or before Jul. 3, 2019 via Internet Archive: Wayback Machine URL<https://web.archive.org/web/20190703062848/https://ultimaker.com/software/ultimaker-cura>, retrieved on Sep. 7, 2021, retrieved from URL<https://ultimaker.com/software/ultimaker-cura>, 11 pages.

Ultimaker.com [online], "Ultimaker S5," available on or before Dec. 12, 2019 via Internet Archive: Wayback Machine URL<https://web.archive.org/web/20191212042119/https://ultimaker.com/3d-printers/ultimaker-s5>, retrieved on Sep. 7, 2021, retrieved from URL<https://ultimaker.com/3d-printers/ultimaker-s5>, 9 pages.

USAB.com [online], "The Basic Jump Shot," dated Oct. 30, 2014, retrieved on Sep. 7, 2021, retrieved from URL<https://www.usab.com/youth/news/2010/01/the-basic-jump-shot.aspx>, 12 pages.

Ziegler-Graham et al., "Estimating the Prevalence of Limb Loss in the United States: 2005 to 2050," Arch. Phys. Med. Rehabilitation, Mar. 2008, 89(3):422-429.

21st Century Kinematics, 1st ed., McCarthy (ed.), 2013, Chapter 7, 28 pages.

Adafruit.com [online], "FLORA—Wearable electronic platform: Arduino-compatible—v3," available on or before Jul. 3, 2014 via Internet Archive: Wayback Machine URL<https://web.archive.org/web/20140703100531/https://www.adafruit.com/product/659>, retrieved on Feb. 10, 2022, retrieved from URL<https://www.adafruit.com/product/659>, 10 pages.

Amazon.com [online], "Mini Electric Linear Actuator Stroke 2"—Force 4.5 lbs—12V | High-Speed 1.97"/sec—Weight 0.15KG Ideal for Intelligent Range Hood, Fan Blades, Cabinets, Window Opener, Robotics, Home Automation," upon information and belief, available no later than Feb. 8, 2022, retrieved on Feb. 10, 2022, retrieved from URL<https://www.amazon.com/dp/B07ZJ4R2NR/ref=twister_B07ZJ7DJ11?_encoding=UTF8&psc=1>, 8 pages.

AMFG.ai [online], "The Additive Manufacturing Industry Landscape 2020: 240 Companies Driving Digital Manufacturing [Updated]," May 26, 2020, retrieved on Feb. 10, 2022, retrieved from URL<https://amfg.ai/2020/05/26/the-additive-manufacturing-industry-landscape-2020-231-companies-driving-digital-manufacturing/>, 11 pages.

Arduino.cc. [online], "Arduino Uno Rev3," available on or before Sep. 1, 2021 via Internet Archive: Wayback Machine URL<https://web.archive.org/web/20210901044607/https://store.arduino.cc/products/arduino-uno-rev3/>, retrieved on Feb. 10, 2022, retrieved from URL<https://store.arduino.cc/products/arduino-uno-rev3/>, 8 pages.

BareConductive.com [online], "Electric Paint," upon information and belief, available no later than Feb. 8, 2022, retrieved on Feb. 10, 2022, retrieved from URL<https://www.bareconductive.com/products/electric-paint?variant=37766230900916>, 9 pages.

BPS Customs [online], "How Keyboards & Mice Are Made—China Factory Tour!," Apr. 10, 2019, retrieved on Feb. 10, 2022, retrieved from URL<https://www.youtube.com/watch?v=GdwkFLLdgYI&ab_channel=BPSCustoms>, 3 pages [video submission].

Burstyn et al., "PrintPut: Resistive and Capacitive Input Widgets for Interactive 3D Prints," Lecture Notes in Computer Science: Human-Computer Interaction—INTERACT 2015, Aug. 30, 2015, 9296:332-339.

Davis et al., "TangibleCircuits: An Interactive 3D Printed Circuit Education Tool for People with Visual Impairments," Presented at Proceedings of the 2020 CHI Conference on Human Factors in Computing Systems, Honolulu, HI, USA, Apr. 25-30, 2020, 13 pages.

EnablingDevices.com [online], "Talkables With Built-in Icon Holders," available on or before Oct. 8, 2019 via Internet Archive: Wayback Machine URL<https://web.archive.org/web/20191008232935/https://enablingdevices.com/product/talkables- wbuilt-in-icon-holders/>, retrieved on Feb. 10, 2022, retrieved from URL<https://enablingdevices.com/product/talkables-wbuilt-in-icon-holders/>, 4 pages.

Flowers et al., "3D printing electronic components and circuits with conductive thermoplastic filament," Additive Manufacturing, Dec. 2017, 18:156-163.

Fuge et al., "The MechProcessor: Helping Novices Design Printable Mechanisms Across Different Printers," Journal of Mechanical Design, Nov. 2015, 137(11):111415, 9 pages.

Gong et al., "MetaSense: Integrating Sensing Capabilities into Mechanical Metamaterial," Presented at Proceedings of The 34th Annual ACM Symposium on User Interface Software and Technology, Virtual Event, USA, Oct. 10-14, 2021, 12 pages.

Götzelmann et al., "CapCodes: Capacitive 3D Printable Identification and On-screen Tracking for Tangible Interaction," Presented at Proceedings of NordiCHI '16: 9th Nordic Conference on Human-Computer Interaction, Gothenburg, Sweden, Oct. 23-27, 2016, 4 pages.

Graphene-Supermarket.com [online], "Graphene Supermarket," available on or before Feb. 2, 2011 via Internet Archive: Wayback Machine URL<https://web.archive.org/web/20110202193004/https://graphene-supermarket.com/home.php>, retrieved on Feb. 10, 2022, retrieved from URL<https://graphene-supermarket.com/home.php>, 2 pages.

Ion et al., "Digital Mechanical Metamaterials," Presented at Proceedings of the Conference on Human Factors in Computing Systems, Denver, CO, USA, May 6-11, 2017, 977-988.

Ion et al., "Metamaterial Mechanisms," Presented at Proceedings of the 29th Annual Symposium on User Interface Software and Technology, Tokyo, Japan, Oct. 16-19, 2016, 529-539.

Iyer et al., "3D printing wireless connected objects," ACM Transactions on Graphics, Nov. 2017, 36(6):242, 13 pages.

Lazarus et al., "3-D Printing Structural Electronics with Conductive Filaments," IEEE Transactions on Components, Packaging and Manufacturing Technology, Nov. 17, 2020, 10(12):1965-1972.

Megaro et al., "A computational design tool for compliant mechanisms," ACM Transactions on Graphics, Jul. 2017, 36(4):82, 12 pages.

Multi3DLLC.com [online], "Electrifi Conductive Filament," available on or before Sep. 13, 2020 via Internet Archive: Wayback Machine URL<https://web.archive.org/web/20200913055553/https://www.multi3dllc.com/product/electrifi/>, retrieved on Feb. 10, 2022, retrieved from URL<https://www.multi3dllc.com/product/electrifi/>, 5 pages.

PopSci.com [online], "The best mechanical keyboards let you game, code, type, and work smoother and faster," Feb. 4, 2021, retrieved on Feb. 10, 2022, retrieved from URL<https://www.popsci.com/story/reviews/best-mechanical-keyboard/>, 5 pages.

Reddit.com [online], "I 3D printed a PCG for Pico.," Feb. 24, 2021, retrieved on Feb. 10, 2022, retrieved from URL<https://www.reddit.com/r/raspberry_pi/comments/lrwymw/i_3d_printed_a_pcb_for_pico/>, 21 pages.

Rhino3D.com [online], "Grasshopper—New in Rhino 6," available on or before Jun. 3, 2019 via Internet Archive: Wayback Machine URL<https://web.archive.org/web/20190603195053/https://www.

(56) References Cited

OTHER PUBLICATIONS rhino3d.com/6/new/grasshopper/>, retrieved on Feb. 10, 2022, retrieved from URL<https://www.rhino3d.com/6/new/grasshopper/>, 6 pages.
Rhino3D.com [online], "Rhinoceros," available on or before Dec. 23, 1996 via Internet Archive: Wayback Machine URL<https://web.archive.org/web/19961223083529/https://www.rhino3d.com/>, retrieved on Feb. 10, 2022, retrieved from URL<https://www.rhino3d.com/>, 2 pages.
Schmitz et al., "Capricate: A fabrication pipeline to design and 3D print capacitive touch sensors for interactive objects," Presented at Proceedings of the 28th Annual ACM Symposium on User Interface Software & Technology, Charlotte, NC, USA, Nov. 8-11, 2015, 253-258.
Schumacher et al., "Microstructures to control elasticity in 3D printing," ACM Transactions on Graphics, Aug. 2015, 34(4):136, 13 pages.
SeeedStudio.com [online], "4A Motor Shield," available on or before Mar. 5, 2018 via Internet Archive: Wayback Machine URL<https://web.archive.org/web/20180305184815/https://wiki.seeedstudio.com/4A_Motor_Shield/>, retrieved on Feb. 10, 2022, retrieved from URL<https://wiki.seeedstudio.com/4A_Motor_Shield/>, 7 pages.
Sparkfun.com [online], "Arduino Mega 2560 R3," available on or before Jan. 8, 2012 via Internet Archive: Wayback Machine URL<https://web.archive.org/web/20120108082715/https://www.sparkfun.com/products/11061>, retrieved on Feb. 10, 2022, retrieved from URL<https://www.sparkfun.com/products/11061>, 17 pages.
Sparkfun.com [online], "Load Cell—200kg, Disc (TAS606)," available on or before Sep. 5, 2015 via Internet Archive: Wayback Machine URL<https://web.archive.org/web/20150905174622/https://www.sparkfun.com/products/13332>, retrieved on Feb. 10, 2022, retrieved from URL<https://www.sparkfun.com/products/13332>, 7 pages.
Takada et al., "MonoTouch: Single capacitive touch sensor that differentiates touch gestures," Presented at Proceedings of the 2016 CHI Conference Extended Abstracts on Human Factors in Computing Systems, San Jose, CA, USA, May 7-12, 2016, 2736-2743.
Thingiverse.com [online], "Mechanical Keyboard—SiCK-68," Mar. 11, 2019, retrieved on Feb. 10, 2022, retrieved from URL<https://www.thingiverse.com/thing:3478494/files>, 3 pages.
Torres et al., "An approach for mechanical property optimization of fused deposition modeling with polylactic acid via design of experiments," Rapid Prototyping Journal, Mar. 21, 2016, 22(2):387-404.
Ultimaker.com [online], "Ultimaker PLA," available on or before May 15, 2020 via Internet Archive: Wayback Machine URL<https://web.archive.org/web/20200515043326/https://ultimaker.com/materials/pla>, retrieved on Feb. 10, 2022, retrieved from URL<https://ultimaker.com/materials/pla>, 5 pages.
Wired.com [online], "Apple's MacBook Pro Gets an All-New Keyboard," Nov. 13, 2019, retrieved on Feb. 10, 2022, retrieved from URL<https://www.wired.com/story/apple-macbook-pro-16-2019/>, 9 pages.
[No Author], "Amputation Data from Community Hospitals," O&P Almanac, Apr. 2016, 1 page.
Adidas.com [online], "4D Shoes & Sneakers," available on or before May 13, 2019 via Internet Archive: Wayback Machine URL<https://web.archive.org/web/20190513141233/https://www.adidas.com/us/4d-shoes>, retrieved on Sep. 15, 2022, retrieved from URL<https://www.adidas.com/us/4d-shoes>, 10 pages.
Bowen et al., "A Low-Cost Customizable Prosthetic Foot with Energy Return Capabilities," Prosthetics and Orthotics Open Journal, Jan. 8, 2018, 2(1:1):1-5.
Brancazio, "Physics of basketball," Am. J. Physics, Jul. 28, 1998, 49(4):356-365.
Chen et al., "Advances in Responsively Conductive Polymer Composites and Sensing Applications," Polym. Reviews, Mar. 10, 2020, 61(1):157-193.
Chiang et al., "Coordination of Basketball Shooting Movement of Different Skill Level Players," Presented at Proceedings of the 24th International Symposium on Biomechanics in Sports, Salzburg, Austria, Jul. 14-18, 2006, 4 pages.
Childers et al., "Increasing prosthetic foot energy return affects whole-body mechanics during walking on level ground and slopes," Sci. Reports, Mar. 29, 2018, 8(1):5354, 12 pages.
Comotti et al., "Multi-Material Design and 3D Printing Method of Lower Limb Prosthetic Sockets," Presented at Proceedings of the 3rd 2015 Workshop on ICTs for Improving Patients Rehabilitation Research Techniques (REHAB '15), Lisbon, Portugal, Oct. 1-2, 2015, 42-45.
Faber et al., "Bioinspired spring origami," Science, Mar. 23, 2018, 359(6382):1386-1391.
Fuss, "Closing the gap through technology," Sports Technology, Nov. 8, 2010, 1(4-5):169-171.
Gao et al., "RevoMaker: Enabling Multi-Directional and Functionally-Embedded 3D Printing Using a Rotational Cuboidal Platform," Presented at Proceedings of the 28th Annual ACM Symposium on User Interface Software & Technology (UIST '15), Charlotte, NC, USA, Nov. 11-15, 2015, 437-446.
Garanger et al., "3D Printing of a Leaf Spring: A Demonstration of Closed-Loop Control in Additive Manufacturing," Presented at Proceedings of the 2018 IEEE Conference on Control Technology and Applications (CCTA), Copenhagen, Denmark, Aug. 21-24, 2018, 465-470.
Gong et al., "MetaSense: Integrating Sensing Capabilities into Mechanical Metamaterial," Presented at Proceedings of the 34th Annual ACM Symposium on User Interface Software and Technology (UIST '21), Virtual Event, USA, Oct. 10-14, 2021, 1063-1073.
Goudswaard et al., "FabriClick: Interweaving Pushbuttons into Fabrics Using 3D Printing and Digital Embroidery," Presented at Proceedings of the 2020 ACM Designing Interactive Systems Conference (DIS '20), Eindhoven, Netherlands, Jul. 6-10, 2020, 379-393.
Grønborg et al., "Conductive Compliant Mechanisms: Geometric tuning of 3D printed flexural sensors," Addit. Manuf. Letters, Sep. 6, 2022, 100088, 15 pages.
Houdijk et al., "Energy storing and return prosthetic feet improve step length symmetry while preserving margins of stability in persons with transtibial amputation," J. Neuroeng. Rehabilitation, Sep. 5, 2018, 15(Suppl 1):76, 8 pages.
Humphreys et al., "The Size and Scope of the Sports Industry in the United States," IASE/NAASE Working Paper Series, Aug. 2008, No. 08-11, 39 pages.
Instructables.com [online], ""Spock" Prosthetic Basketball Hand," upon information and belief, available no later than Oct. 16, 2020, retrieved on Sep. 15, 2022, retrieved from URL<https://www.instructables.com/Spock-Prosthetic-Basketball-Hand-by-UCLA-3D4E/>, 19 pages.
Leigh et al., "A Simple, Low-Cost Conductive Composite Material for 3D Printing of Electronic Sensors," PLoS One, Nov. 21, 2012, 7(11):e49365, 6 pages.
Malone et al., "Shooting mechanics related to player classification and free throw success in wheelchair basketball," J. Rehabil. Res. Development, Nov./Dec. 2002, 39(6):701-709.
Nolan, "Carbon fibre prostheses and running in amputees: A review," Foot Ankle Surgery, Jul. 14, 2008, 14(3):125-129.
Okubo et al., "Rebounds of basketball field shots," Sports Engineering, Oct. 14, 2014, 18(1):43-54.
Olesnavage et al., "Analysis of Rollover Shape and Energy Storage and Return in Cantilever Beam-Type Prosthetic Feet," Presented at Proceedings of the ASME 2014 International Design Engineering Technical Conferences and Computers and Information in Engineering Conference (IDETC/CIE 2014), Buffalo, NY, USA, Aug. 17-20, 2014, 10 pages.
OpenBionics.com [online], "Meet the Hero Arm—a prosthetic arm for adults and children," available on or before Mar. 30, 2018 via Internet Archive: Wayback Machine URL<https://web.archive.org/web/20180330052341/https://openbionics.com/hero-arm/>, retrieved on Sep. 15, 2022, retrieved from URL<https://openbionics.com/hero-arm/>, 20 pages.
Podmenik et al., "The effect of shooting range on the dynamics of limbs angular velocities of the basketball shot," Kinesiology, 2017, 49(1):92-100.

(56) References Cited

OTHER PUBLICATIONS

Ray et al., "Prosthetic energy return during walking increases after 3 weeks of adaptation to a new device," J. Neuroeng. Rehabilitation, Jan. 27, 2018, 15(1):6, 8 pages.
Rocha et al., "Fabrication and characterization of bending and pressure sensors for a soft prosthetic hand," J. Micromech. Microengineering, Jan. 17, 2018, 28(3):034001, 24 pages.
Rojas et al., "Kinematic adjustments in the basketball jump shot against an opponent," Ergonomics, Oct. 2000, 43(10):135-144.
Saggio et al., "Flex sensor characterization against shape and curvature changes," Sens. Actuator A Physical, Apr. 15, 2018, 273:221-231.
Shigleys Mechanical Engineering Design, 11th ed., Budynas et al. (eds.), 2019, 1116 pages.
TRSProsthetics.com [online], "Body Powered Prosthetic Simulator," available on or before Dec. 22, 2015 via Internet Archive: Wayback Machine URL<https://web.archive.org/web/20151222233207/https://www.trsprosthetics.com/product/body-powered-prosthetic-simulator/>, retrieved on Sep. 15, 2022, retrieved from URL<https://www.trsprosthetics.com/product/body-powered-prosthetic-simulator/>, 4 pages.
TRSProsthetics.com [online], "Sports—Prosthetics for Sports & Activities," available on or before Dec. 13, 2015 via Internet Archive: Wayback Machine URL<https://web.archive.org/web/20151213154816/http://www.trsprosthetics.com/shop-category/sports/>, retrieved on Sep. 15, 2022, retrieved from URL<https://www.trsprosthetics.com/shop-category/sports/>, 9 pages.
Ultimaker.com [online], "Ultimaker TPU 95A," available on or before Jun. 17, 2020, via Internet Archive: Wayback Machine URL<https://web.archive.org/web/20200617042640/https://ultimaker.com/materials/tpu-95a>, retrieved on Sep. 15, 2022, retrieved from URL<https://ultimaker.com/materials/tpu-95a>, 4 pages.
Walker et al., "Recreational Terminal Devices for Children With Upper Extremity Amputations," J. Pediatr. Orthopedics, Mar. 2008, 28(2):271-273.
Wolterink et al., "A 3D-Printed Soft Fingertip Sensor for Providing Information about Normal and Shear Components of Interaction Forces," Sensors, Jun. 22, 2021, 21(13):4271, 13 pages.
Wright et al., "Prosthetic usage in major upper extremity amputations," J. Hand Surgery, Jul. 1, 1995, 20(4):619-622.
Yoshii et al., "Measurement of wrist flexion and extension torques in different forearm positions," Biomed. Eng. Online, Dec. 12, 2015, 14:115, 10 pages.
Zelik et al., "Systematic Variation of Prosthetic Foot Spring Affects Center-of-Mass Mechanics and Metabolic Cost During Walking," IEEE Trans. Neural Syst. Rehabil. Engineering, Aug. 2011, 19(4):411-419.
Zolfagharian et al., "3D printing non-assembly compliant joints for soft robotics," Results in Engineering, Sep. 2022, 15:100558, 10 pages.

* cited by examiner

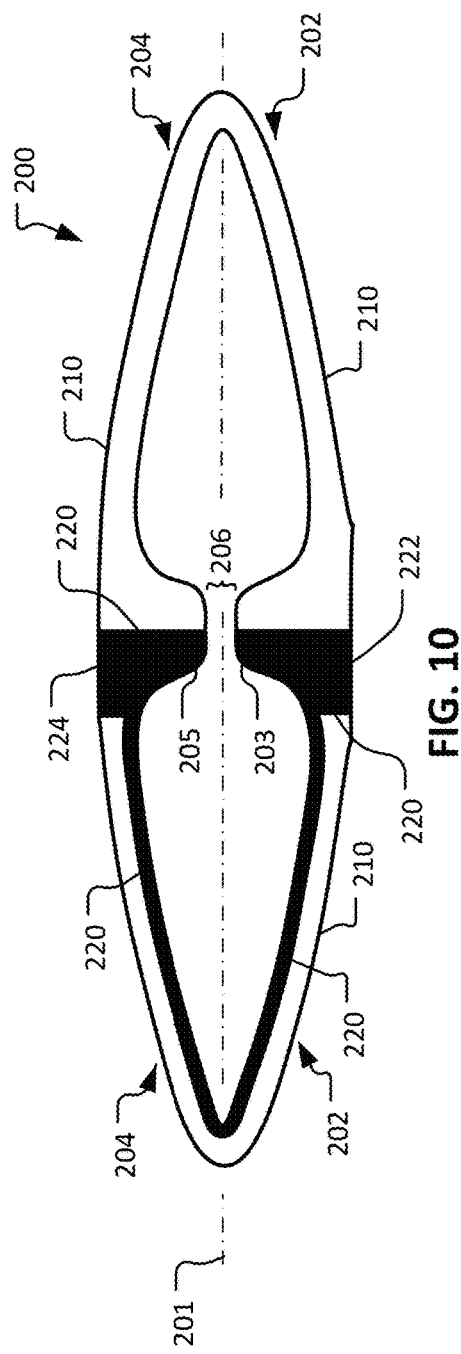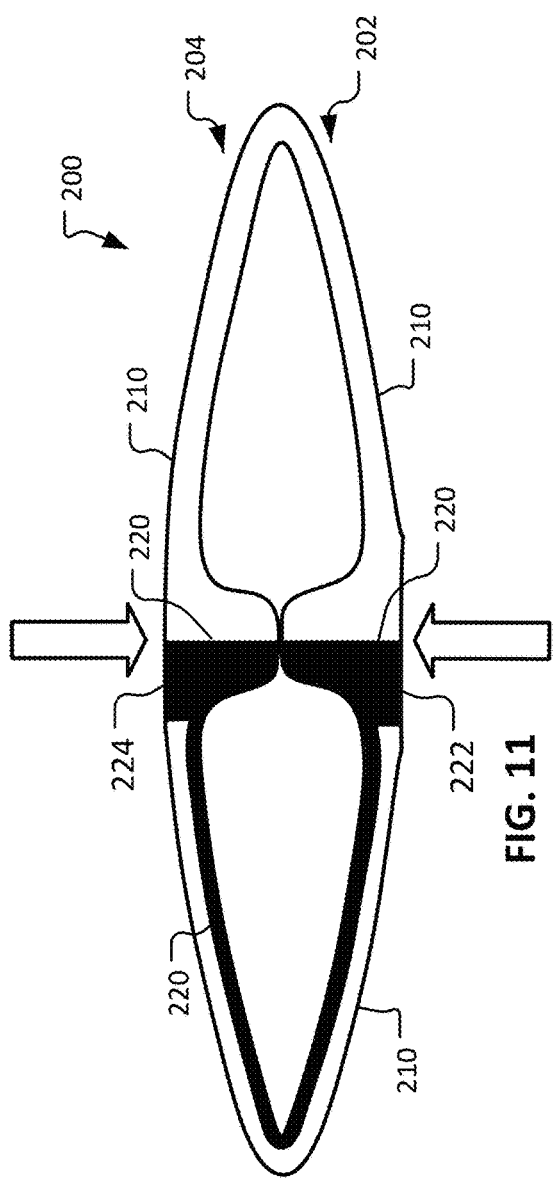

SPRINGS WITH STRAIN FEEDBACK

CROSS-REFERENCE TO RELATED APPLICATIONS

This application claims the benefit of U.S. Provisional Application Ser. No. 63/092,688 filed Oct. 16, 2020. The disclosure of the prior application is considered part of (and is incorporated by reference in) the disclosure of this application.

TECHNICAL FIELD

This disclosure generally relates to springs.

BACKGROUND 3D printing is a widely used manufacturing technique for both commercial products and research across many industries with emerging research areas in multi-material 3D printing, metamaterials, and 3D printed electronics. Because of the high customizability and accessibility 3D printing offers, more mechanisms are being 3D printed.

SUMMARY

In general, an aspect of the subject matter described in this specification relates to springs that provide energy return and have a conductivity that changes in relation to an amount of strain or deformation of the spring. In some embodiments, the springs are made by 3D printing (additive manufacturing). Such springs made by 3D printing may include a material that is electrically conductive and, optionally, another material that is electrically non-conductive (insulative). When both conductive material and insulative material are included, such springs can be made by multi-material 3D printing in some embodiments. The extent of the deformation or strain of the spring may be determined or estimated by measuring the conductivity or resistivity of the electrically conductive material portion of the spring.

Some inventive aspects described herein include: (i) creating customizable 3D printed springs with integrated strain sensing, (ii) combining multi-material 3D printing, 3D printed electronics, springs, compliant design and electrical feedback, and (iii) the use of 3D printed strain sensing springs for various practical applications. A spring with an integrated strain sensing system may reduce the number of electronic components, reduce the steps for assembly after fabrication, and reduce the weight and overall cost in comparison to other techniques such as the use of a traditional accelerometer or pressure sensor.

In one aspect, this disclosure is directed to a spring that includes a first 3D printed material and a second 3D printed material integrated with the first 3D printed material. The second 3D printed material has an electrical conductivity that is greater than an electrical conductivity of the first 3D printed material. The spring also includes a first electrical contact connected to the second 3D printed material, and a second electrical contact connected to the second 3D printed material. The spring is configured to have an electrical conductivity between the first and second electrical contacts that changes in response to deformation of the spring.

Such a spring may optionally include one or more of the following features. The deformation of the spring may deform each of the first and second 3D printed materials. The spring may be a coil spring. The spring may be a cantilever spring. The changes of the electrical conductivity in response to the deformation of the spring may be proportional to the deformation of the spring. The changes of the electrical conductivity in response to the deformation of the spring may include a one or more step changes. The second 3D printed material between the first and second electrical contacts may comprise a portion of an outer surface of the spring. The second 3D printed material between the first and second electrical contacts may be encapsulated within the first 3D printed material. The second 3D printed material may be between the first and second electrical contacts.

In another aspect, this disclosure is directed to a method of making a spring. The method includes using a multi-material 3D printing process to form a first material and a second material into a spring shape. The second material can have an electrical conductivity that is greater than an electrical conductivity of the first material. Elastic deformations of the spring can be detected by measuring the electrical conductivity of the second material.

Such a method of making a spring may optionally include one or more of the following features. The multi-material 3D printing process may be a dual extrusion process. During at least some portions of the forming, the first and second materials may be deposited concurrently. At multiple cross-sections of the spring, the first material may comprise a first portion of an outer periphery of the spring and the second material may comprise a second portion of the outer periphery of the spring. At multiple cross-sections of the spring, the second material may be entirely encapsulated within the first material. The spring may include only the second material at multiple cross-sections of the spring. The spring shape may be a coil spring. The spring shape may be a cantilevered spring.

In another aspect, this disclosure is directed to a spring that includes a 3D printed material having an electrical conductivity and an infill density percentage of less than 100%. The spring also includes a first electrical contact connected to the 3D printed material, and a second electrical contact connected to the 3D printed material. The spring is configured to have an electrical conductivity between the first and second electrical contacts that changes in response to deformation of the spring.

In another aspect, this disclosure is directed to a spring that includes a first spring segment having a first spring constant, an uncompressed configuration, a partially compressed configuration, and a fully compressed configuration. The spring also includes a second spring segment having a second spring constant, an uncompressed configuration, a partially compressed configuration, and a fully compressed configuration. The second spring constant is greater than the first spring constant. The first and second spring segments are arranged in series. A first electrical circuit between a first electrical contact on the first spring segment and a second electrical contact on the second spring segment has a first resistivity when: (i) the first spring segment is in the uncompressed configuration, and (ii) the first spring segment is in the partially compressed configuration, and wherein the first electrical circuit has a second resistivity when the first spring segment is in the fully compressed configuration. The first resistivity is greater than the second resistivity.

Such a spring may optionally include one or more of the following features. The first electrical circuit may have a third resistivity when the first spring segment is in the fully compressed configuration and the second spring segment is in the fully compressed configuration. The third resistivity may be less than the second resistivity. In some embodiments, the spring is a multi-material 3D printed spring.

The details of one or more implementations are set forth in the accompanying drawings and the description, below. Other potential features and advantages of the disclosure will be apparent from the description and drawings, and from the claims.

BRIEF DESCRIPTION OF THE DRAWINGS

FIG. 10 illustrates another example spring in accordance with some embodiments.

FIG. 11 illustrates the spring of FIG. 10 in a fully compressed configuration.

Like reference symbols in the various drawings indicate like elements.

DETAILED DESCRIPTION

Figure 2:
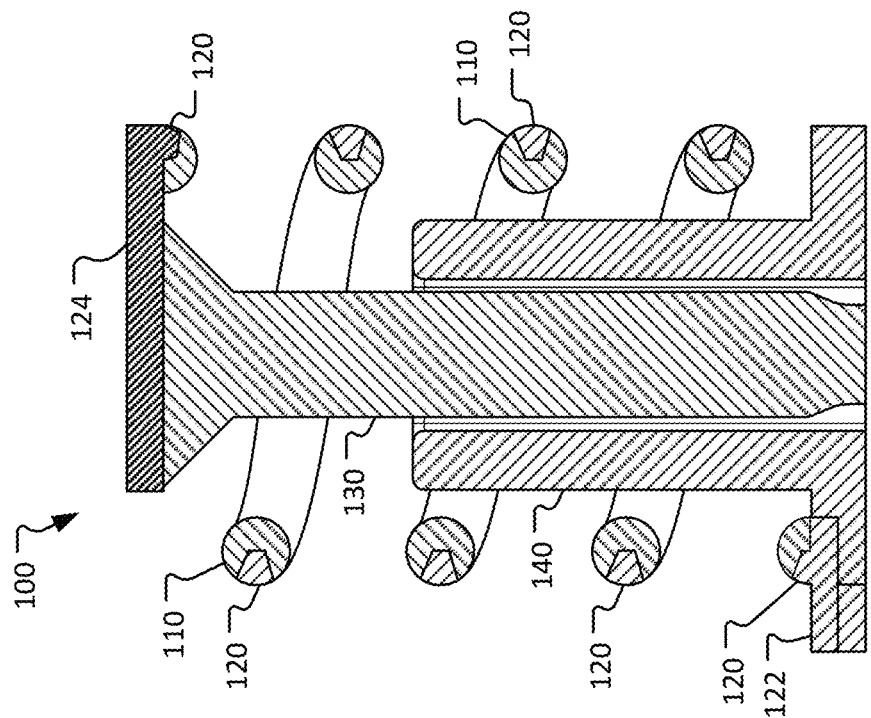
FIG. 2 is a longitudinal cross-sectional view of the spring of FIG. 1.
Figure 1:
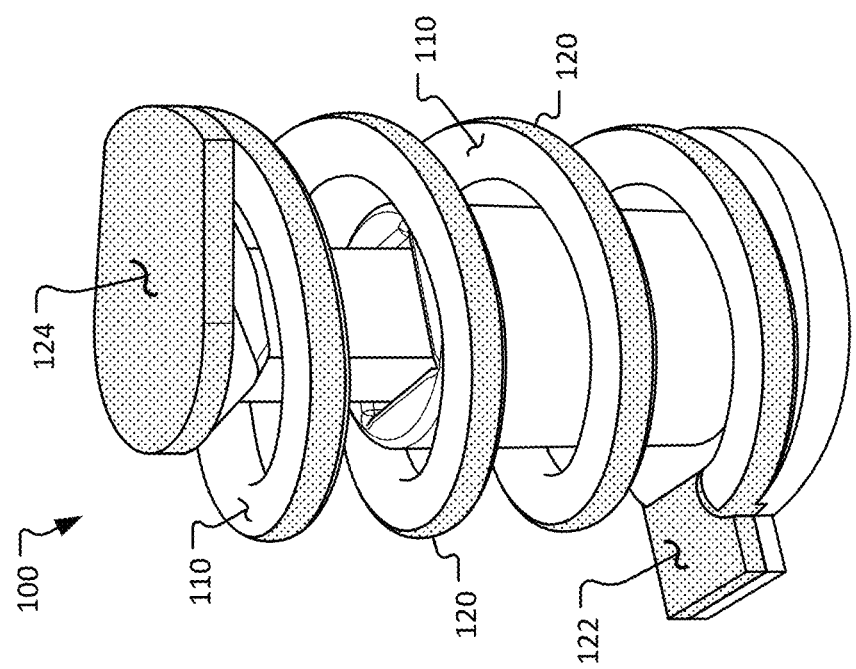
FIG. 1 is a perspective view of an example spring in accordance with some embodiments.

Referring to FIGS. 1 and 2, an example spring 100 can be configured to have an electrical conductivity that changes in response to deformations of the spring 100. In other words, the spring 100 can provide an integrated strain sensing capability in addition to providing energy return.

In the depicted embodiment, the spring 100 is made of at least two different materials. For example, the spring 100 includes a first material 110 and a second material 120. The first material 110 and the second material 120 have differing electrical properties. For example, in some embodiments the second material 120 has an electrical conductivity that is greater than an electrical conductivity of the first material 110. In some embodiments, the first material 110 is an electrical insulator and the second material 120 is an electrical conductor.

The example spring 100 is a compression spring. It should be understood, however, that the concepts described herein can also be implemented in many other types of springs. For example, the concepts described herein can be implemented in other types of springs such as, but not limited to, extension springs, torsion springs, cantilevered springs, leaf springs, variable rate springs, constant force springs, constant rate springs, and the like, without limitation. The example spring 100 can be configured to have any desired spring property including, but not limited to, spring rate, numbers of coils, coil member diameter, pitch, inner and outer diameter of the spring coils, free length, solid length, end types, and the like. Moreover, these springs can be tuned to generate different desired spring rates and/or force profiles by changing the properties of the spring 100 as defined by Hooke's Law and Castigliano's theorem. For example, by changing the cross-sectional thickness, the spring diameter, and/or the number of turns (which affect the spring's Young's modulus and shear modulus of a coil spring), the properties of the spring 100 can be changed. Accordingly, the spring 100 has the potential to be tuned for a specific end use.

The spring 100 also includes a first electrical contact 122 and a second electrical contact 124. The first electrical contact 122 and the second electrical contact 124 are each in electrical communication with the second material 120. At least a portion of the second material 120 extends between the first electrical contact 122 and the second electrical contact 124. In some embodiments, an entirety of the second material 120 extends between the first electrical contact 122 and the second electrical contact 124. In particular embodiments (such as the depicted embodiment), the first electrical contact 122 and the second electrical contact 124 are made of the same type of material as the second material 120. In such a case, the second material 120 and the contacts 122 and 124 are made as a continuous unitary member. In some embodiments, the first electrical contact 122 and/or the second electrical contact 124 are made of a different type of material than the second material 120.

In some embodiments, the spring 100 is, or comprises, a 3D printed spring or a multi-material 3D printed spring. For example, the first material 110 can be a first 3D printed material, and the second material 120 can be a second 3D printed material that is integrated with the first 3D printed material. In some cases, during at least some portions of the multi-material 3D printing process to make the spring 100, the first material 110 and the second material 120 are deposited concurrently or simultaneously.

3D printing is a manufacturing technique with emerging areas of research in multi-material 3D printing, metamaterials, and 3D printed electronics. Such techniques can be used to form the spring 100. The high customizability of a multi-material 3D printing process can make such a process well suited to making the spring 100 and other types of springs that include integrated strain sensing in keeping with the principles described herein.

A multi-material 3D printed object (e.g., such as the spring 100 with its first material 110 and second material 120) may refer to an object printed with multiple materials by a multi-material 3D printer. Multi-material 3D printers are capable of consistently printing with multiple materials in the same print. When printing, the material properties of a part are at least somewhat dictated by the material properties of the materials it is printed with.

Metamaterials are a class of materials that expand on this capability by allowing parts printed with only one material to have different material properties in multiple sections of the part. This is possible by changing the geometry and internal structure of the print. Metamaterials can enable printing compliant mechanisms and deformable structures without the need for multiple parts. A key application of 3D printed deformable objects is tunable 3D printed helical springs, such as the spring 100. 3D printing springs introduces the possibility of printing not only deformable objects, but objects with energy return properties. In addition, new materials enable 3D printed electronics. These materials allow for 3D prints to act as sensors, transmitters, and conductive traces without the need for additional electronics minimizing the number of components required, assembly time, weight, and cost.

When a 3D model is imported into a slicing software, G-code for the toolpath of the print head is created layer by layer. Generally, when parts with multiple materials are 3D printed at the same time, individual parts must be placed in the slicing software and the toolpath is created for each material requiring the designer to understand how the two parts interact. Alternatively, a custom design tool can be created to enable technology to eliminate such requirements.

Figure 3:
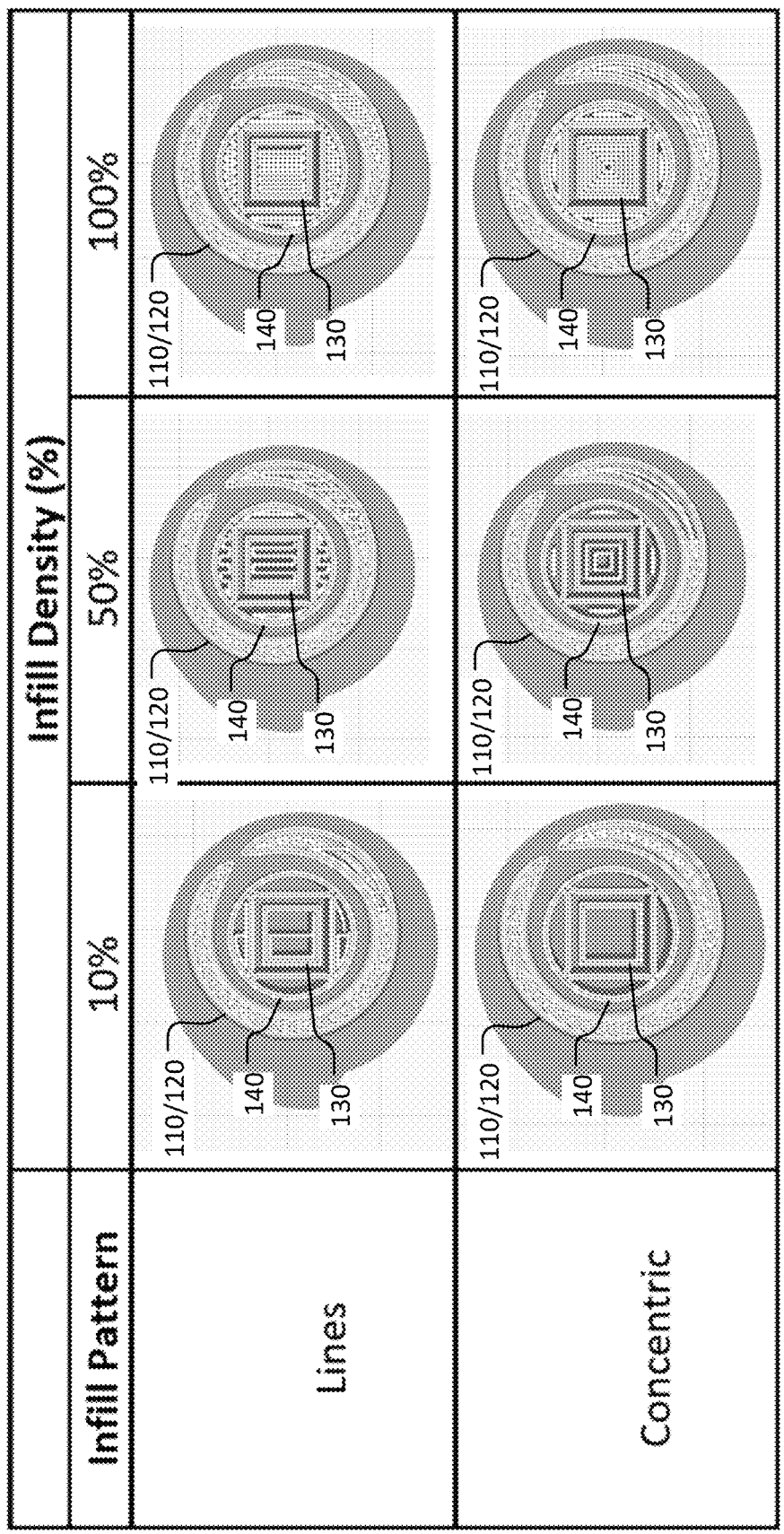
FIG. 3 is a chart showing transverse cross-sectional views of the spring of FIG. 1 that have been 3D printed using various example combinations of infill densities and infill patterns.

Material properties for individual 3D printed parts such as the spring 100 can be changed by modifying parameters such as, but not limited to, the type of material, infill density, and/or infill pattern. For example, FIG. 3 illustrates six different simulated transverse cross-sectional views of the spring 100 that were modeled for 3D printing using various exemplary combinations of infill density (10%, 50%, and 100%) and infill pattern (lines and concentric). Accordingly, it can be understood that such parameters can be chosen for the spring 100 to provide desired properties of the spring 100.

Figure 5:
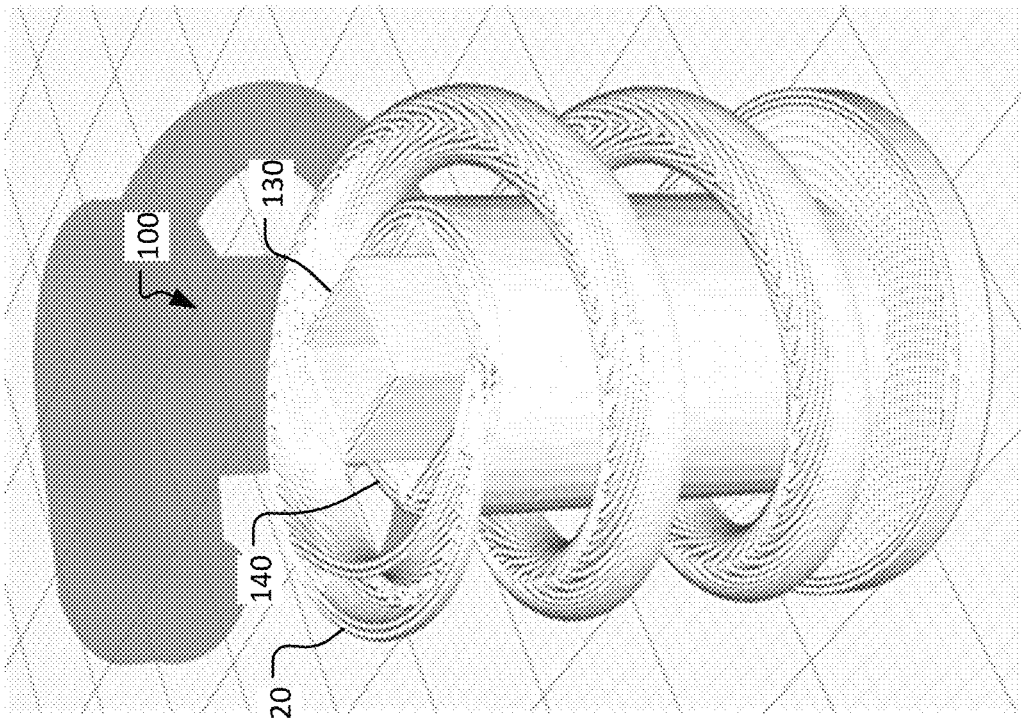
FIGS. 4 and 5 illustrate two different transverse cross-sectional views of the spring of FIG. 1 that has been 3D printed in an example manner using an axial infill density gradient.
Figure 4:
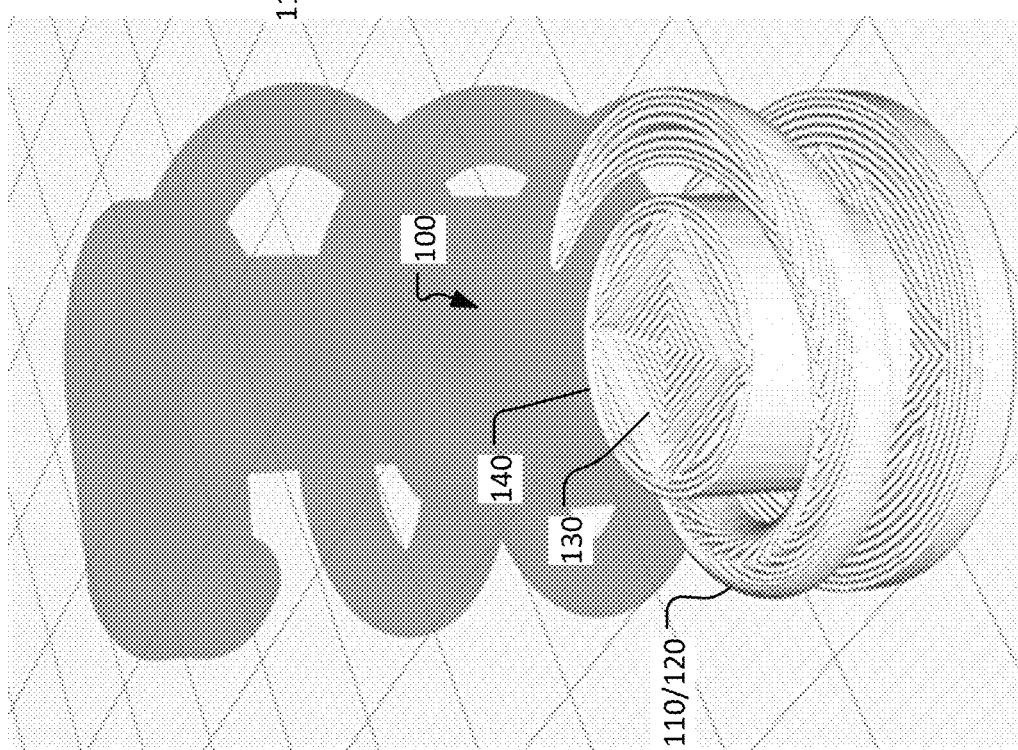

Moreover, as illustrated in FIGS. 4 and 5, the spring 100 can be 3D printed in such a manner that the spring 100 has different properties at various positions along the central axis of the spring 100. For example, in these images we see that the infill density of the coil 110/120 is higher at the cross-section shown in FIG. 4 than in the cross-section shown in FIG. 5. In the depicted example, the same is true of the shaft 130 (however, in some embodiments the shaft 130 can maintain a consistent infill density along its entire length). That is, the infill density has a higher percentage at the cross-section shown in FIG. 4 than in the cross-section shown in FIG. 5. These examples illustrate that properties of the spring 100, and/or various portions of the spring 100, can be selected/determined by the strategic selection of parameters of the 3D printing process. In some embodiments, various portions of the spring 100 can have differing infill densities at the same cross-sectional location.

Rather than modifying structures layer by layer, some software allows for parts to be customized voxel by voxel. A voxel is 3D unit of measurement rather than a 2D layer of a print. Having a robust understanding of how materials will be printed is additionally important when designing 3D printed electronics.

Broadly, metamaterials and compliant mechanisms are a new class of 3D printed objects where the material properties of the component are defined by the internal geometry and structure of the object, and not by the material itself. Metamaterial assemblies allow for a single part to have multiple mechanical properties in the same print. Because of this, full products can be printed in one print reducing the need for assembling a product after printing.

Still referring to FIGS. 1 and 2, in some implementations, such as the spring 100, a conductive material (e.g., from a carbon based filament) is printed at the same print as traditional material(s) (e.g., from non-conductive filaments). For example, in some embodiments the spring 100 can be formed by using a multi-material 3D printing process where the first material 110 is made from one or more non-conductive materials and the second material 120 is made from one or more conductive materials (e.g., from one or more carbon-based conductive PLA filaments, conductive liquid, etc.).

As described further below, the spring 100 is capable of integrated strain sensing. The data from the spring 100 can be used as either a binary signal or an analog signal.

The depicted spring 100 also includes a shaft 130 and a guide sleeve 140. The shaft 130 is attached to one end of the spring 100 and the guide sleeve 140 is attached to the opposite end of the spring 100. The shaft 130 movably slides within an internal space defined by the guide sleeve 140. In some embodiments, including the shaft 130 and the guide sleeve 140 can advantageously prevent the spring 100 from buckling when compressed. These components, while beneficial in some embodiments, are optional.

In the depicted embodiment, the shaft 130 has a polygonal cross-sectional shape and the cross-sectional shape of the internal space defined by the guide sleeve 140 has a corresponding shape (to create a sliding fit therebetween). The polygonal cross-sectional shapes prevent rotations of the shaft 130 relative to the guide sleeve 140. In the depicted embodiment, the polygonal cross-sectional shape is rectangular. However, other polygonal cross-sectional shapes and non-polygonal cross-sectional shapes can also be used in some embodiments of the spring 100.

The spring 100 is made for absorbing compression and for providing energy return as the spring 100 rebounds from being compressed. When the spring 100 is compressed, its coils elastically deform. The deformations of the coils naturally result in stresses and strains in the materials of the coils of the spring 100 (i.e., the first material 110 and the second material 120). In the depicted embodiment of the spring 100, both the first material 110 and the second material 120 deform when the spring 100 is compressed.

The electrical resistance of a conductive material (e.g., the second material 120 in this example) varies with changes in strain of the material. Accordingly, the extent of the deformation of the spring 100 can be determined or estimated by monitoring the electrical resistance (or conductivity) of the second material 120 which is strained as the spring 100 is compressed and/or rebounds from being compressed. In some embodiments, the changes of the electrical resistance/conductivity in response to the deformation of the spring 100 are proportional to the extent of deformation of the spring 100.

The first electrical contact 122 and the second electrical contact 124 are in electrical communication with the second material 120. While the first electrical contact 122 and the second electrical contact 124 are at the ends of the second material 120 in the depicted embodiment, in some embodiments first electrical contact 122 and/or the second electrical contact 124 is/are at locations along the second electrical contact 124. At least a portion of the second material 120 (in the coils of the spring 100) extends between the first electrical contact 122 and the second electrical contact 124.

The second material 120 inherently has a certain conductivity or resistivity. That conductivity or resistivity varies as the second material 120 is strained or deformed. Accordingly, it follows that the spring 100 is configured to have an electrical conductivity/resistivity between the first electrical contact 122 and the second electrical contact 124 that changes in response to deformation of the spring 100. It also follows that by measuring or monitoring the electrical conductivity between the first electrical contact 122 and the second electrical contact 124, the extent of the deformation of the spring 100 can be determined or estimated.

Figure 8:
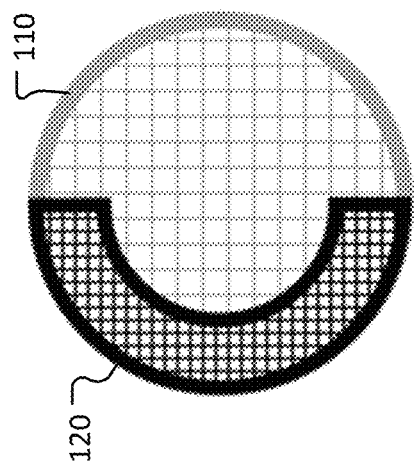
FIG. 8 is a transverse cross-sectional view of another example coil of the spring of FIG. 1.
Figure 7:
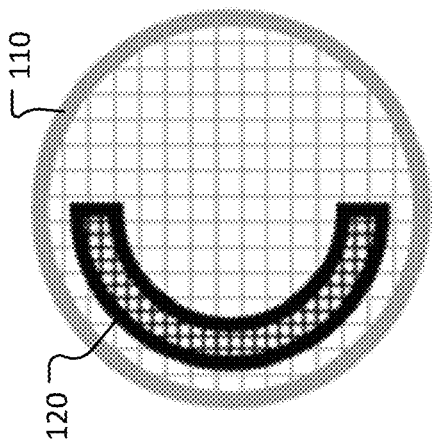
FIG. 7 is a transverse cross-sectional view of another example coil of the spring of FIG. 1.
Figure 6:
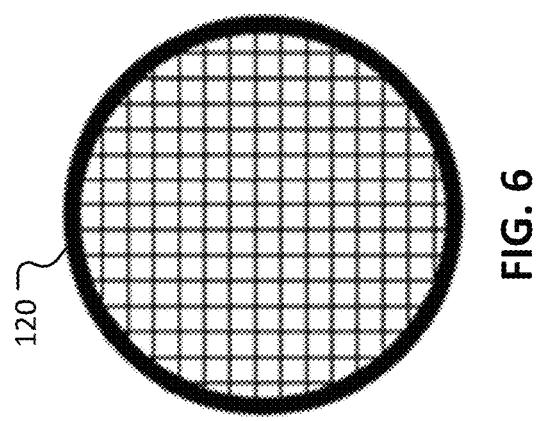
FIG. 6 is a transverse cross-sectional view of an example coil of the spring of FIG. 1.

The materials that make up the 3D printed spring 100 can be configured in many different ways. For example, FIGS. 6-8 show some non-limiting example cross sections of the 3D printed spring 100. In some embodiments, the cross-sectional configuration of the material(s) of the spring 100 is consistent all along the coils of the spring 100. In particular embodiments, the cross-sectional configuration of the material(s) of the spring 100 (or the infill density) varies along the coils of the spring 100 (e.g., the material(s) can be arranged in two of more differing configurations at separate locations along the coils of the spring 100). Multiple sensor architectures can be used for different applications. Printing with a triangular infill over lines may yield a stiffer spring, and both mechanical and electrical properties may be optimized further to achieve the most elastic response from the coil spring 100 and the largest and most predictable reading from the integrated strain gauge. In some embodiments, infill printing can be performed using other patterns such as, but not limited to, hexagonal, zig-zag, and concentric. This may be made possible by printing the core of a spring with a conductive material that has one infill pattern and density, then a traditional PLA or other material as a shell with a different infill pattern and density for advantageous mechanical properties.

FIG. 6 shows the cross-section of a coil of the spring 100 that is 3D printed exclusively using the second material 120 (the conductive material) and 100% infill. That is, in some embodiments only the second 3D printed material 120 is between the first electrical contact 122 and the second electrical contact 124. This configuration works well for the highest conductivity to transmit a signal, but may experience little or no change in resistance under loading/strain/deformation. Resistance may increase if the infill percentage is lowered, due to a smaller cross sectional area of conductive material. These implementations may provide more of a digital output than an analog output. Using conductive materials with various conductivities and by tuning their infill density percentage and pattern, the desired digital or analog response of the system can be tuned. In some cases, because the carbon-based PLA (the second material 120) has such high conductivity, the coil spring 100 may not produce a change in resistance throughout the full range of compression. Instead, a change in resistance may only be detected when the coil spring 100 is fully compressed, FIG. 7 shows an example cross-section in which, to protect the conductive trace of the second 3D printed material 120 from external elements, the conductive trace is printed inside the walls of the first material 110 (e.g., inside the walls of the traditional PLA filament). In other words, the second 3D printed material 120 is encapsulated within the first 3D printed material 110 at one or more locations (or entirely) between the first electrical contact 122 and the second electrical contact 124. By changing the infill density and pattern of the conductive PLA filament (the second 3D printed material 120), the stiffness or spring constant of the spring 100 can be adjusted.

FIG. 8 shows another example cross-section of the coil of the spring 100. In this example, the printing of the conductive material (the second 3D printed material 120) comprises an outer portion/segment of the coil, and the rest of the coil is printed with the first 3D printed material 110 (e.g., traditional PLA). In other words, the second 3D printed material 120 between the first electrical contact 122 and the second electrical contact 124 comprises a portion of an outer surface of the spring 100. In the depicted embodiment, the second material 120 comprises about 50% of the outer surface of the coil, and the first material 110 comprises the other 50%. In some embodiments, the second material 120 comprises a majority of the outer surface of the coil. In some embodiments, the first material 110 comprises a majority of the outer surface of the coil (e.g., see FIG. 2). This configuration may be desirable for transmitting a signal through the second material 120 of the coil spring 100 (e.g., to act as a strain gauge) while retaining the mechanical material properties of the first material 110 (the other non-conductive material) for desired spring characteristics.

In some embodiments, to generate a more analog response (e.g., where the change in resistivity/conductivity of the second material 120 is more directly proportional to the deformation of the spring 100), conductive PLA filament may be embedded not only in the coil spring, but in other locations such as in a prismatic joint as well. In some embodiments, a desired linear response, desired exponential response, or another type of desired analog response from deformation of the spring 100 can be tuned by selecting the design of the conductive trace of the second material 120, such as by altering the cross sectional area or infill percentage. By placing the strain sensor in the prismatic joint, the mechanical material properties of the coil spring 100 may be tuned to exactly what the application calls for while reading cleaner signals from the sensor. Inspiration may be taken from metamaterials, but by designing open linkages.

Figure 9:
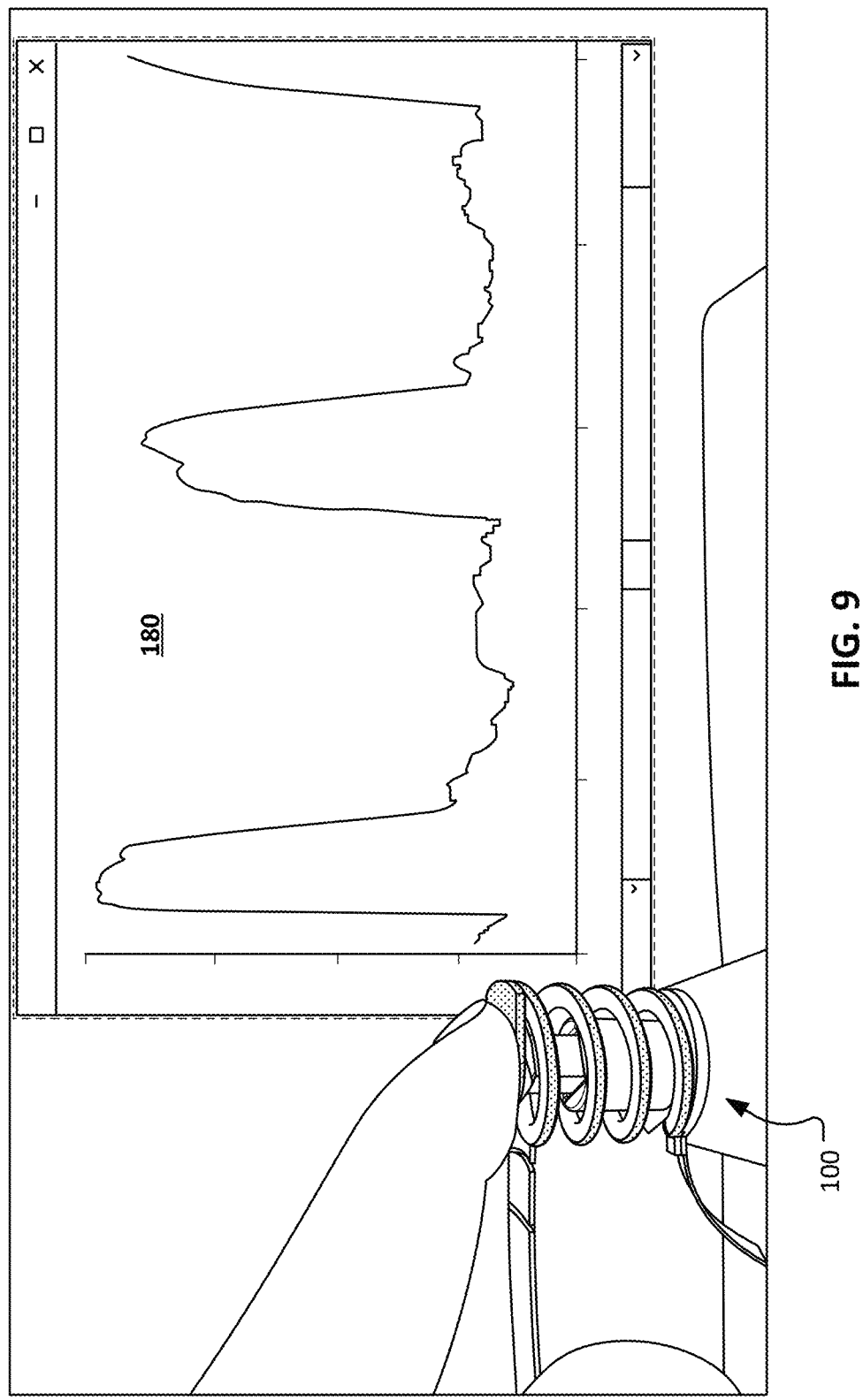
FIG. 9 illustrates that the deformation of the springs described herein may be determined or estimated by measuring the conductivity or resistivity of the spring material.

FIG. 9 illustrates that deformations of the spring 100 that cause a change in the conductivity/resistivity of the second material 120 can be used to provide an electrical signal for various useful purposes. In this example, variances of the electrical signal (in response to variances in the deformation of the spring 100) are shown in a plot 180. The x-axis of the plot 180 is time and the y-axis is a signal output from the spring 100 that is responsive to, and indicative of, the deformations of the spring 100. FIG. 9 shows the change in resistance of the coil spring 100 during a cycle of relaxation, compression, and relaxation.

In some embodiments, a Wheatstone bridge is used in conjunction with the spring 100 to provide a variable voltage output from the spring 100 that is responsive or proportional to the strain of the second material 120 (and responsive or proportional to the deformation of the spring 100).

Strain may be measured through a change in resistance of the conductive coil (the second material 120) of the spring 100. In some embodiments, the resistance may be read through the analog input of an Adafruit Metro Mini 328 microcontroller and smoothed using a moving average filter with a window size of 10, for example.

FIGS. 10 and 11 illustrate another example type of spring 200 that can output a signal that is responsive to deformations of the spring 200. The configuration of the spring 200 may be referred to as a platform leaf spring, elliptic spring, and the like.

The spring 200 is a type of compression spring. The spring 200 is shown in a natural uncompressed configuration in FIG. 10, and a fully compressed configuration in FIG. 11. Of course, there are also an infinite number of partially compressed configurations between the uncompressed configuration (FIG. 10) and the fully compressed configuration (FIG. 10).

The spring 200 includes a first bow spring 202 and a second bow spring 204. The first bow spring 202 and the second bow spring 204 oppose each other in terms of their respective curvatures. In the depicted embodiment, a central axis 201 divides the first bow spring 202 and the second bow spring 204. The first bow spring 202 can be a mirror image of the second bow spring 204, but that is not a requirement of all embodiments of the spring 200. While not visible in these 2-dimensional illustrations, it should be understood that the spring 200 is a 3-dimensional object with a depth (i.e., into and/or out of the paper on which FIGS. 10 and 11 are shown). The spring 200 is elastically deformable, as described further below, and has a spring constant.

The spring constant of the spring 200 can be adjusted by various factors including, but not limited to, material choice, material infill parameters, and/or by the selected geometry of the spring 200. For example, the length or thickness of the first bow spring 202 and/or the second bow spring 204 can be increased or decreased to adjust the spring 200 to a particular spring rate.

In the natural uncompressed configuration as shown in FIG. 10, a gap 206 exists between a contact portion 203 of the first bow spring 202 and contact portion 205 of the second bow spring 204. In the fully compressed configuration as shown in FIG. 11, there is no gap between the contact portions 203 and 205 of the first bow spring 202 and the second bow spring 204. Instead, the contact portions 203 and 205 of the first bow spring 202 and the second bow spring 204 are in contact with each other, which defines the fully compressed configuration. While the spring 200 is in any of the partially compressed configurations, the contact portions 203 and 205 are not in contact with each other. The opposed arrows shown in FIG. 11 represent the force that is necessary to compress the spring 200 to the fully compressed configuration.

In a manner that is very analogous to the spring 100 described above, in some embodiments the spring 200 can be made of two or more materials. For example, the spring 200 can be made of a first material 210 that is electrically insulative and a second material 220 that is electrically conductive. In order to distinguish between the first material 210 that is electrically insulative from the second material 220 that is electrically conductive, in these figures the second material 220 is shown in a gray shade, whereas the first material 210 is not shaded. In some embodiments, the spring 200 can be made by a multi-material 3D printing process to integrally form the first material 210 and the second material 220 into the spring shape as shown. In particular embodiments, the spring 200 can be made by other processes, such as injection molding, machining, forming, and the like.

The second material 220 that is electrically conductive comprises a portion of the first bow spring 202, and also a portion of the second bow spring 204. These portions of the second material 220 are depicted by the gray shaded areas. The depicted arrangement of the first material 210 that is electrically insulative and the second material 220 that is electrically conductive provides one non-limiting example of many different arrangements that can be used to create the spring 200 with the functionalities described herein.

The second material 220 that is electrically conductive is exposed on the opposing faces of each of the contact portions 203 and 205 of the first bow spring 202 and the second bow spring 204. Accordingly, when the opposing faces of each of the contact portions 203 and 205 make contact with each other in the fully compressed configuration (FIG. 11), the second material 220 of the first bow spring 202 becomes directly electrically connected and communicative with the second material 220 of the second bow spring 204 via the contact portions 203 and 205.

The spring 200 also has a first electrical contact 222 and a second electrical contact 224. The first electrical contact 222 and the second electrical contact 224 are each in electrical communication with the second material 220. The first electrical contact 222 is on the first bow spring 202. The second electrical contact 224 is on the second bow spring 204.

In all configurations of the spring 200, an electrically conductive path exists between the first electrical contact 222 and the second electrical contact 224. That is, in all configurations of the spring 200 the first electrical contact 222 and the second electrical contact 224 are in electrical communication with each other via the second material 220 that is electrically conductive. However, the particular electrically conductive pathway between the first electrical contact 222 and the second electrical contact 224 differs on the basis of whether the spring 200 is in: (i) the fully compressed configuration shown in FIG. 11 or (ii) the natural uncompressed configuration as shown in FIG. 10 (and in all of the partially compressed configurations).

In the natural uncompressed configuration as shown in FIG. 10 (and in all of the partially compressed configurations), the contact portions 203 and 205 of the second material 220 are not in direct contact with each other. Accordingly, the electrically conductive path between the first electrical contact 222 and the second electrical contact 224 while the spring 200 is in the natural uncompressed configuration extends along the full length of the second material 220 (which, in the depicted embodiment, is about one half of the length and/or width of the first bow spring 202 and one half of the length of the second bow spring 204). In contrast, when the spring 200 is in the fully compressed configuration as shown in FIG. 11, the contact portions 203 and 205 of the first bow spring 202 and the second bow spring 204 are in contact with each other, and the electrically conductive path between the first electrical contact 222 and the second electrical contact 224 therefore extends directly therebetween via the contact portions 203 and 205. That is the case because electricity tends to flow along the path of least resistance. The path between the first electrical contact 222 and the second electrical contact 224 via the contact portions 203 and 205 has less electrical resistance than the path between the first electrical contact 222 and the second electrical contact 224 that extends along the full length of the second material 220. Accordingly, the electrically conductive path between the first electrical contact 222 and the second electrical contact 224 extends directly therebetween via the contact portions 203 and 205 while the spring 200 is in the fully compressed configuration.

As described above, the electrical pathway between the first electrical contact 222 and the second electrical contact 224 is longer when the spring 200 is in the natural uncompressed configuration as shown in FIG. 10 (and in all of the partially compressed configurations) than when the spring 200 is in the fully compressed configuration as shown in FIG. 11. Accordingly, because the second material 220 is not a perfect conductor, it follows that the electrical resistance of the electrical pathway between the first electrical contact 222 and the second electrical contact 224 is greater when the spring 200 is in the natural uncompressed configuration (and in all of the partially compressed configurations) than when the spring 200 is in the fully compressed configuration.

The electrical resistance between the first electrical contact 222 and the second electrical contact 224 can be determined, measured, and/or monitored. This can provide a way to electrically monitor and determine the mechanical configurations or deformation status of the spring 200. For example, a step change in the electrical resistance between the first electrical contact 222 and the second electrical contact 224 will occur when the spring 200 transitions into the fully compressed configuration and when the spring 200 transitions out of the fully compressed configuration. In particular, a step change reduction in the electrical resistance between the first electrical contact 222 and the second electrical contact 224 will occur when the spring 200 transitions into the fully compressed configuration, and a step change increase in the electrical resistance between the first electrical contact 222 and the second electrical contact 224 will occur when the spring 200 transitions out of the fully compressed configuration.

In contrast to the spring 100 described above that provides an analog electrical output that is reflective or proportional to the extent of the deformation of the spring 100, in some embodiments the spring 200 provides a digital output (or a step change).

For clarity and simplicity of the description hereafter, the resistance between the first electrical contact 222 and the second electrical contact 224 while the spring 200 is in the fully compressed configuration will be referred to as "1×," and the resistance between the first electrical contact 222 and the second electrical contact 224 while the spring 200 is in the uncompressed configuration (or in any partially compressed configuration) will be referred to as "2×." This nomenclature is being used merely to indicate that the electrical resistance between the first electrical contact 222 and the second electrical contact 224 is less when the when the spring 200 is in the fully compressed configuration than when the spring 200 is in an uncompressed or partially compressed configuration. The nomenclature should not be interpreted as requiring the electrical resistance between the first electrical contact 222 and the second electrical contact 224 to be doubled when the spring 200 transitions out of the fully compressed configuration (although that can be the case in some embodiments). In fact, various parameters of the spring 200 can be adjusted to provide virtually any desired amount of change in the electrical resistance between the first electrical contact 222 and the second electrical contact 224 when the spring 200 transitions into and out of the fully compressed configuration.

Figure 12:
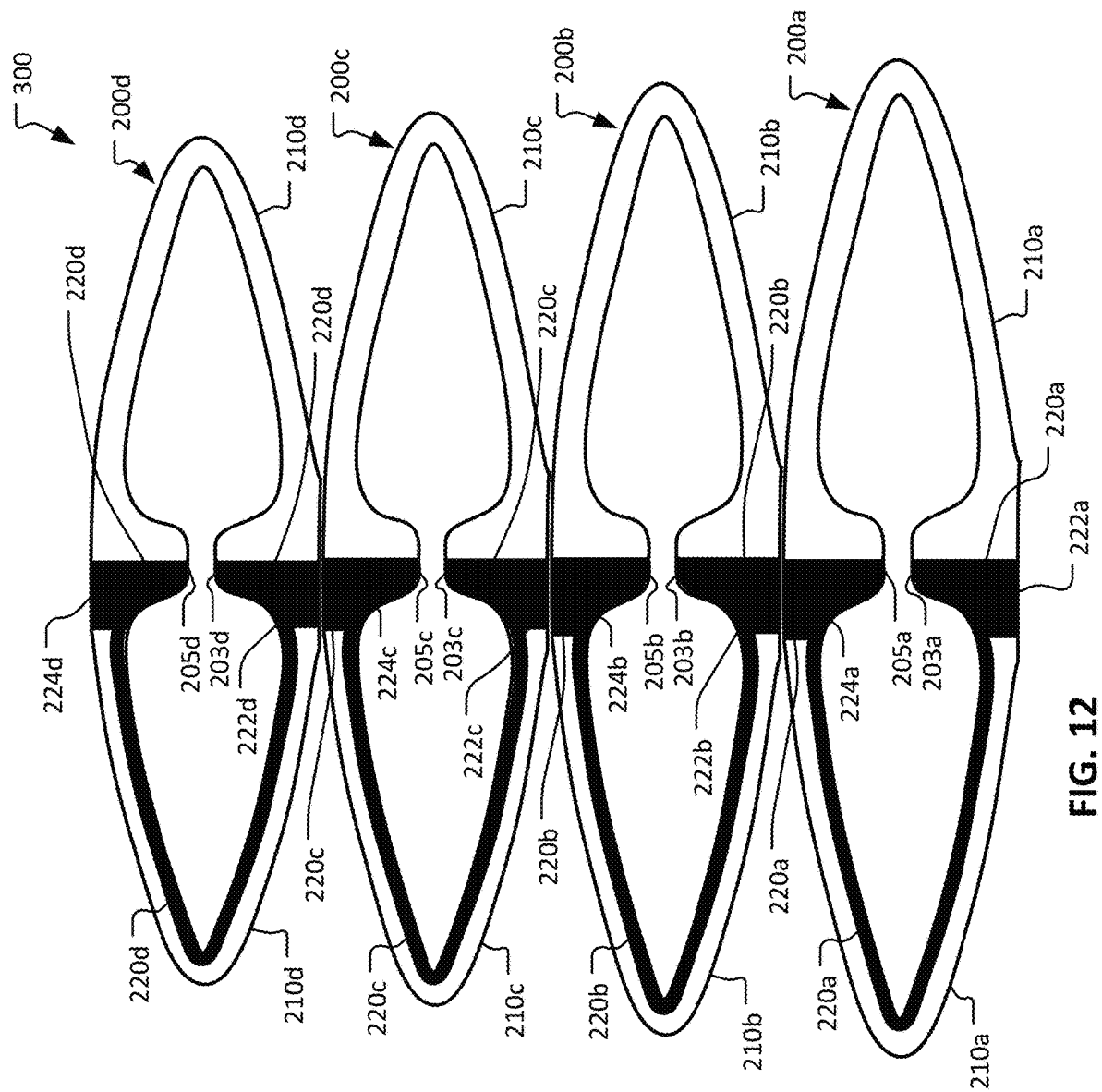
FIG. 12 illustrates an example spring that has multiple spring segments that are each configured like the spring of FIG. 10, but with differing spring constants. The multiple segments are arranged in series.

Referring to FIG. 12, an example progressive rate spring 300 can be constructed by arranging multiple springs 200 in a series configuration. The depicted example spring 300 includes four platform leaf springs 200a, 200b, 200c, and 200d (collectively springs 200a-d) arranged in series. The multiple springs 200a-d can also be individually referred to as spring segments 200a-d. While the spring 300 includes four platform leaf springs 200a-d (or four spring segments 200a-d), in some embodiments two, three, five, six, seven, eight, or more than eight of the spring segments can be included.

In some embodiments, the spring rates of the spring segments 200a-d differ from each other. For example, in the depicted embodiment the spring rate of spring segment 200a is the least, the spring rate of spring segment 200b is the second lowest, the spring rate of spring segment 200c is the third lowest (higher than the spring rates of spring segments 200a and 200b), and the spring rate of spring segment 200d is the highest (higher than spring segments 200a-c).

The differing spring rates of the individual springs 200a-d advantageously ensure that the contact portions of the individual springs 200a-d do not make contact at the same time/stage as the spring 300 is compressed. Instead, the contact portions of the individual springs 200a-d will make contact at different times sequentially, as described further below.

In some embodiments, the gaps between the contact portions can be selected to cause the contact portions of the individual springs 200a-d to make contact at different times/stages during the compression of the spring 300. In other words, the gaps between the contact portions of some individual springs can be made with longer distances to cause the contact portions of those individual springs to make contact at later stages during the compression process of the spring 300.

The spring 300 includes multiple electrical contacts. Each individual spring 200a-d includes a respective first electrical contact 222a-d and a respective second electrical contact 224a-d. Because of the depicted stacked arrangement of the individual spring segments 200a-d, the second electrical contact 224a of the first spring segment 200a is in contact with the first electrical contact 222b of the second spring segment 200b. In addition, the second electrical contact 224b of the second spring segment 200b is in contact with the first electrical contact 222c of the third spring segment 200c. In addition, the second electrical contact 224c of the third spring segment 200c is in contact with the first electrical contact 222d of the fourth spring segment 200d.

When the spring 300 is in its uncompressed configuration (e.g., as depicted in FIG. 12), the first electrical contact 222a of the first spring segment 200a is in electrical communication with the second electrical contact 224d of the fourth spring segment 200d. The same is true when the spring 300 is in a partially compressed configuration (when none of the contact portions of the individual spring segments 200a-d have made contact). In the uncompressed configuration of the spring 300, the electrical path between the first electrical contact 222a of the first spring segment 200a and the second electrical contact 224d of the fourth spring segment 200d extends through the full lengths of the second materials 220a-d of each individual spring 200a-d. Accordingly, it can be said that the resistance between the first electrical contact 222a of the first spring segment 200a and the second electrical contact 224d of the fourth spring segment 200d equals 8×. The resistance of 8× is the sum total of the 2× resistance of each of the four individual springs 200a-d. Thus, a measured resistance of 8× between the first electrical contact 222a of the first spring segment 200a and the second electrical contact 224d of the fourth spring segment 200d indicates that none of the individual springs 200a-d are fully compressed.

Figure 14:
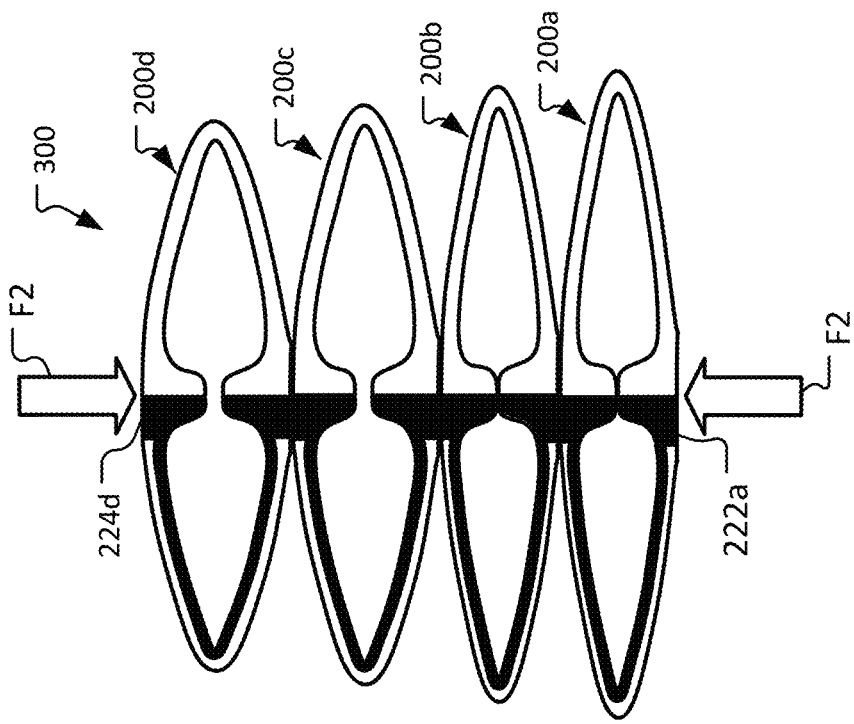
FIG. 14 illustrates the spring of FIG. 12 with two of the spring segments in fully compressed configurations and the other spring segments in partially compressed configurations.
Figure 13:
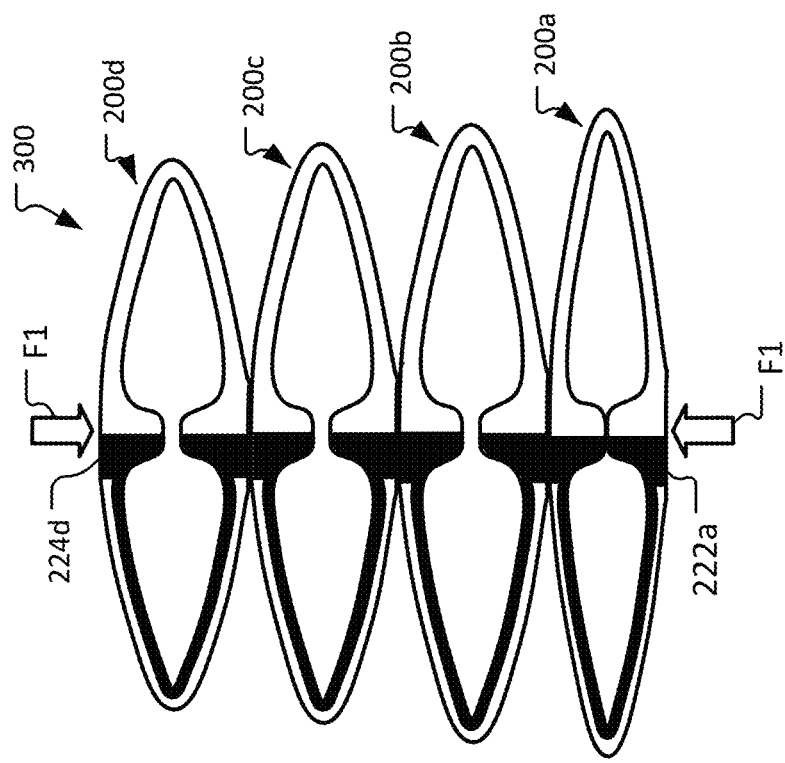
FIG. 13 illustrates the spring of FIG. 12 with one of the spring segments in a fully compressed configuration and the other spring segments in partially compressed configurations.
Figure 16:
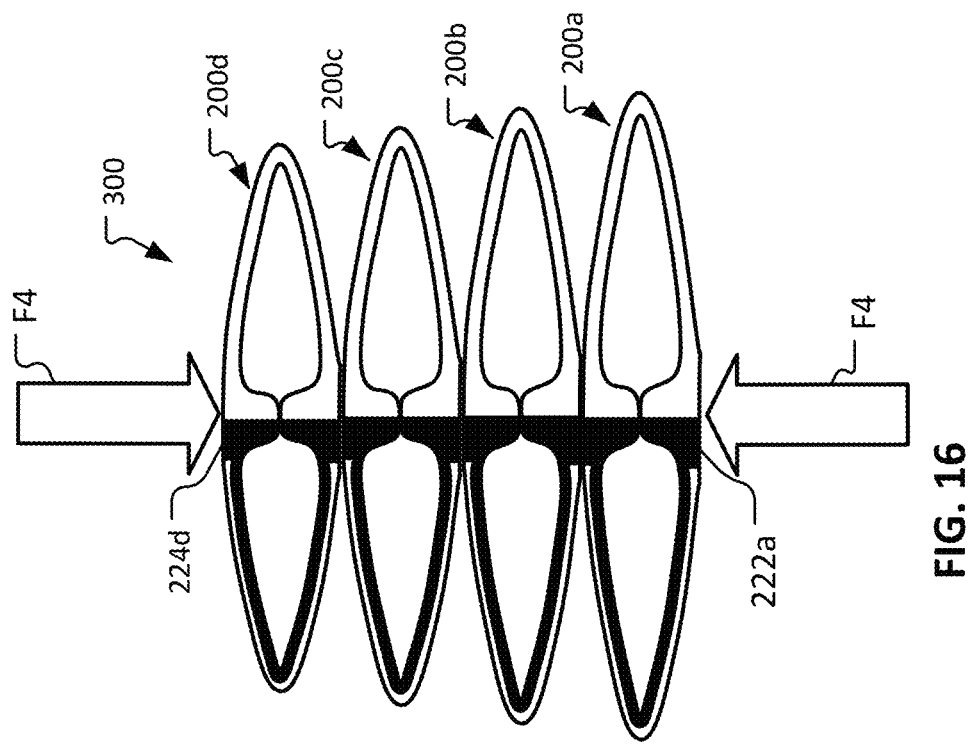
FIG. 16 illustrates the spring of FIG. 12 with all of the spring segments in fully compressed configurations.
Figure 15:
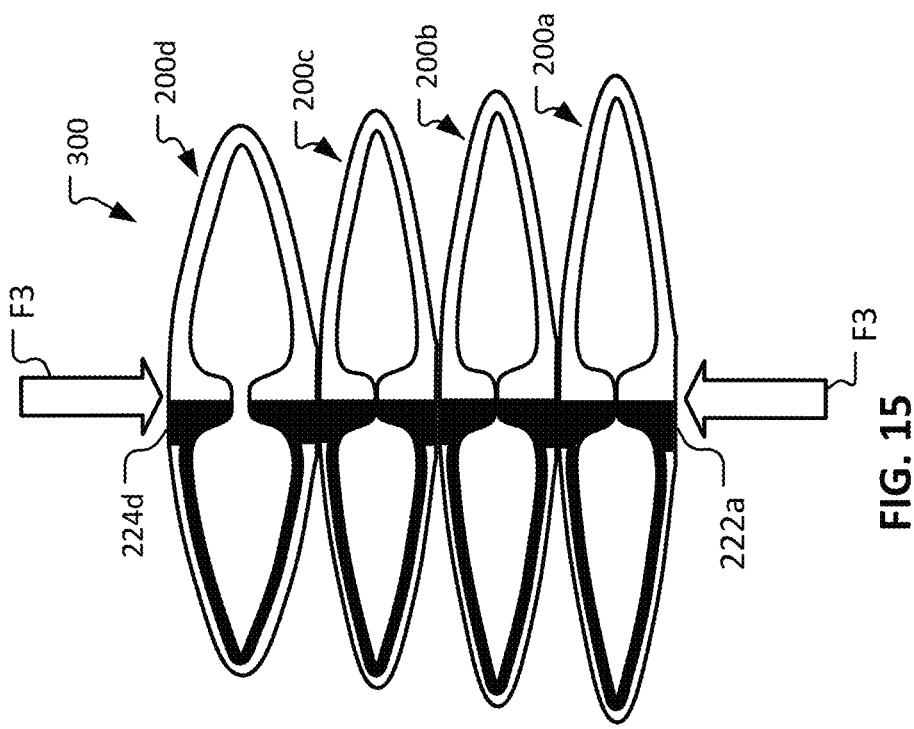
FIG. 15 illustrates the spring of FIG. 12 with three of the spring segments in fully compressed configurations and the remaining spring segment in a partially compressed configuration.

Referring now also to FIGS. 13-16 that are a series of figures that illustrate the steps of a progressive compression process of the spring 300. In FIG. 13, a compressive force F1 is applied to the spring 300. In FIG. 14, a compressive force F2 is applied to the spring 300. In FIG. 15, a compressive force F3 is applied to the spring 300. In FIG. 16, a compressive force F4 is applied to the spring 300. The compressive forces are related to each other according to: F1<F2<F3<F4.

In FIG. 13, the magnitude of force F1 is enough to compress the first spring segment 200a to its fully compressed configuration, but not enough to compress any of the other spring segments 200b-d to their fully compressed configurations. Instead, the force F1 only partially compresses the other spring segments 200b-d. In this configuration of the spring 300, direct contact is established between the contact portions 203a and 205a of the first spring segment 200a. The direct contact between the contact portions 203a and 205a causes the resistance of the first spring segment 200a between the first electrical contact 222a and the second electrical contact 224a to become 1×. The total resistance of the spring 300 (between the first electrical contact 222a of the first spring segment 200a and the second electrical contact 224d of the fourth spring segment 200d) is 7×. The resistance of 7× is the sum total of the resistances of each of the spring segments 200a-d, wherein the resistance of the first spring segment 200a is 1× and the resistance of the other three segments are 2× each.

The measurement of a total electrical resistance of 7× (between the first electrical contact 222a of the first spring segment 200a and the second electrical contact 224d of the fourth spring segment 200d) provides an electrical indication that the first spring segment 200a is fully compressed, and that the other spring segments 200b-d are not fully compressed. Accordingly, in this manner the electrical output(s) of the spring 300 provide an indication of the extent of the mechanical compression/deformation of the spring 300.

In FIG. 14, the magnitude of force F2 is enough to compress the first spring segment 200a and the second spring segment 200b to their fully compressed configurations, but not enough to compress the third spring segment 200c and the fourth spring segment 200d to their fully compressed configurations. Instead, the force F2 only partially compresses the third spring segment 200c and the fourth spring segment 200d. In this configuration of the spring 300, direct contact is established between: (i) the contact portions 203a and 205a of the first spring segment 200a and (ii) the contact portions 203b and 205b of the second spring segment 200b. The direct contact between the contact portions 203a and 205a causes the resistance of the first spring segment 200a between the first electrical contact 222a and the second electrical contact 224a to become 1×. The direct contact between the contact portions 203b and 205b causes the resistance of the second spring segment 200b between the first electrical contact 222b and the second electrical contact 224b to become 1×. The total resistance of the spring 300 (between the first electrical contact 222a of the first spring segment 200a and the second electrical contact 224d of the fourth spring segment 200d) is 6×. The resistance of 6× is the sum total of the resistances of each of the spring segments 200a-d, wherein the resistances of the first spring segment 200a and the second spring segment 200b are 1× each, and the resistance of the other two segments are 2× each.

The measurement of a total electrical resistance of 6× (between the first electrical contact 222a of the first spring segment 200a and the second electrical contact 224d of the fourth spring segment 200d) provides an electrical indication that the first spring segment 200a and the second spring segment 200b are fully compressed, and that the third spring segment 200c and the fourth spring segment 200d are not fully compressed. Accordingly, in this manner the electrical output(s) of the spring 300 provide an indication of the extent of the mechanical compression/deformation of the spring 300.

In FIG. 15, the magnitude of force F3 is enough to compress the first spring segment 200a, the second spring segment 200b, and the third spring segment 200c to their fully compressed configurations, but still not enough to compress the fourth spring segment 200d to its fully compressed configuration. Instead, the force F3 only partially compresses the fourth spring segment 200d. In this configuration of the spring 300, direct contact is established between: (i) the contact portions 203a and 205a of the first spring segment 200a, (ii) the contact portions 203b and 205b of the second spring segment 200b, and (iii) the contact portions 203c and 205c of the third spring segment 200c. The direct contact between the contact portions 203a and 205a causes the resistance of the first spring segment 200a between the first electrical contact 222a and the second electrical contact 224a to become 1×. The direct contact between the contact portions 203b and 205b causes the resistance of the second spring segment 200b between the first electrical contact 222b and the second electrical contact 224b to become 1×. The direct contact between the contact portions 203c and 205c causes the resistance of the third spring segment 200c between the first electrical contact 222c and the second electrical contact 224c to become 1×. The total resistance of the spring 300 (between the first electrical contact 222a of the first spring segment 200a and the second electrical contact 224d of the fourth spring segment 200d) is 5×. The resistance of 5× is the sum total of the resistances of each of the spring segments 200a-d, wherein the resistances of the first spring segment 200a, the second spring segment 200b, and the third spring segment 200c are 1× each, and the resistance of the fourth spring segment 200d is 2×.

The measurement of a total electrical resistance of 5× (between the first electrical contact 222a of the first spring segment 200a and the second electrical contact 224d of the fourth spring segment 200d) provides an electrical indication that the first spring segment 200a, the second spring segment 200b, and the third spring segment 200c are fully compressed, and that the fourth spring segment 200d is not fully compressed. Accordingly, in this manner the electrical output(s) of the spring 300 provide an indication of the extent of the mechanical compression/deformation of the spring 300.

In FIG. 16, the magnitude of force F4 is enough to compress the first spring segment 200a, the second spring segment 200b, the third spring segment 200c, and the fourth spring segment 200d to their fully compressed configurations. In other words, the magnitude of force F4 is enough to compress the spring 300 to its fully compressed configuration. In this configuration of the spring 300, an electrical circuit is established between: (i) the contact portions 203a and 205a of the first spring segment 200a, (ii) the contact portions 203b and 205b of the second spring segment 200b, (iii) the contact portions 203c and 205c of the third spring segment 200b, and (iv) the contact portions 203d and 205d of the fourth spring segment 200d. The direct contact between the contact portions 203a and 205a causes the resistance of the first spring segment 200a between the first electrical contact 222a and the second electrical contact 224a to become 1×. The direct contact between the contact portions 203b and 205b causes the resistance of the second spring segment 200b between the first electrical contact 222b and the second electrical contact 224b to become 1×. The direct contact between the contact portions 203c and 205c causes the resistance of the third spring segment 200c between the first electrical contact 222c and the second electrical contact 224c to become 1×. The direct contact between the contact portions 203d and 205d causes the resistance of the fourth spring segment 200d between the first electrical contact 222d and the second electrical contact 224d to become 1×. The total resistance of the spring 300 (between the first electrical contact 222a of the first spring segment 200a and the second electrical contact 224d of the fourth spring segment 200d) is 4×. The resistance of 4× is the sum total of the resistances of each of the spring segments 200a-d, wherein the resistances of the first spring segment 200a, the second spring segment 200b, the third spring segment 200c, and the fourth spring segment 200d are 1× each.

The measurement of a total electrical resistance of 4× (between the first electrical contact 222a of the first spring segment 200a and the second electrical contact 224d of the fourth spring segment 200d) provides an electrical indication that the first spring segment 200a, the second spring segment 200b, the third spring segment 200c, and the fourth spring segment 200d are all fully compressed. Accordingly, in this manner the electrical output(s) of the spring 300 provide an indication of the extent of the mechanical compression/deformation of the spring 300.

The electrical indications provided by the spring 300 as described above in reference to series of FIGS. 12-16 can be referred to as multiple step changes that indicate the extent of the deformation of the spring 300.

Figure 18:
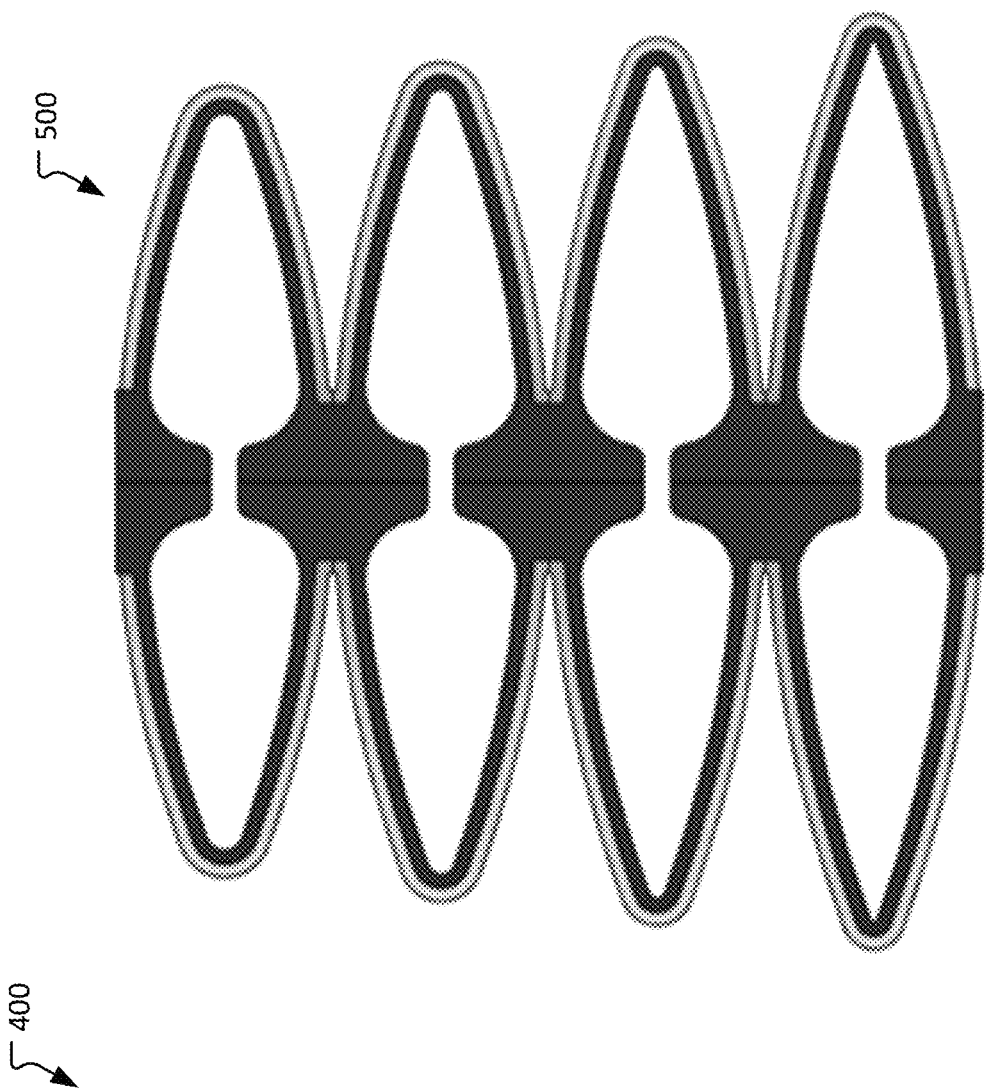
FIG. 18 illustrates another example spring in accordance with some embodiments.
Figure 17:
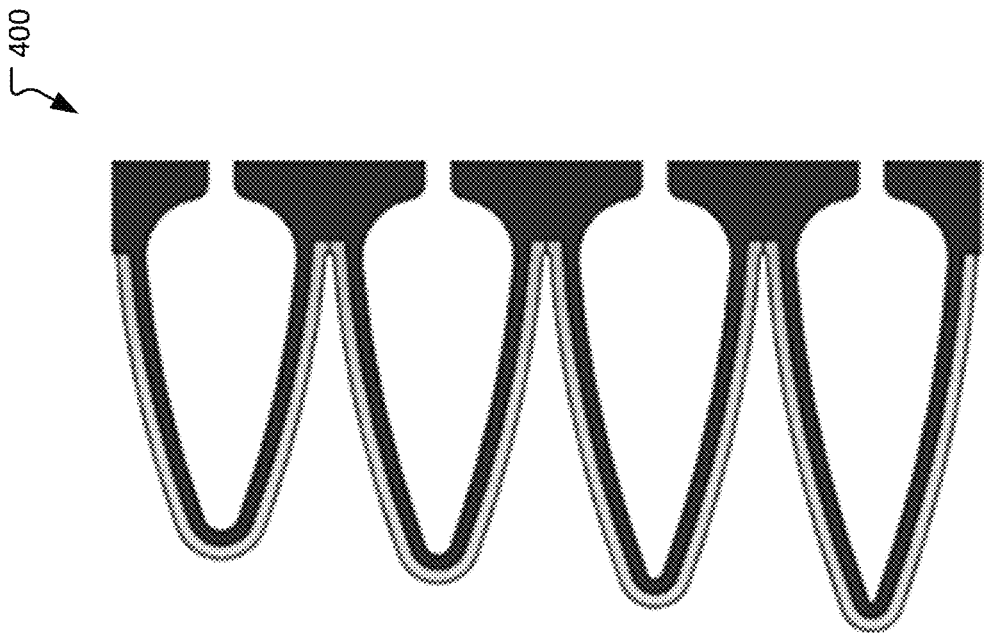
FIG. 17 illustrates another example spring in accordance with some embodiments.
Figure 19:
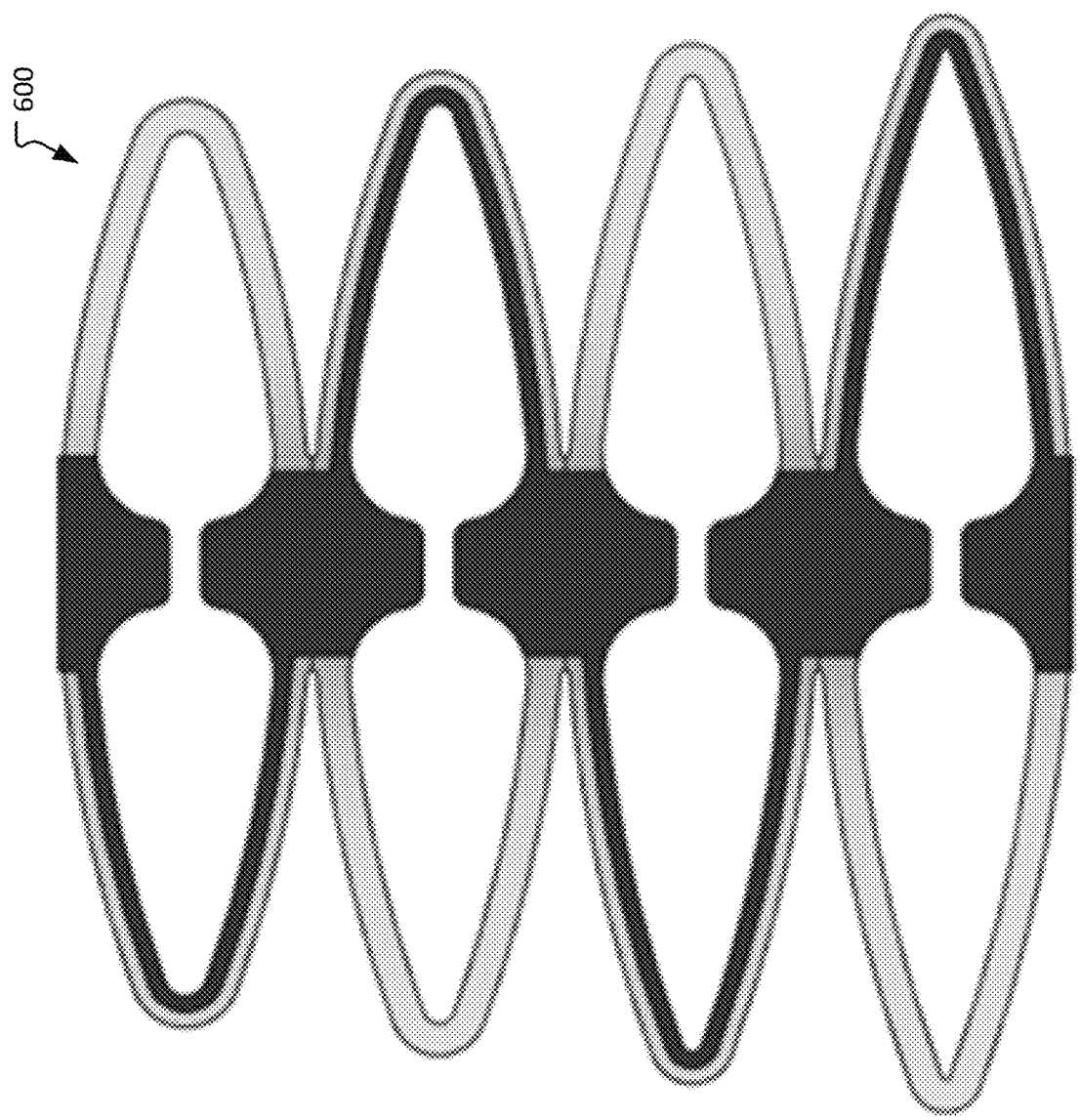
FIG. 19 illustrates another example spring in accordance with some embodiments.

There are many possible variations of springs that can function in essentially the same manner as the spring 300 as described above. Some examples of such variations are depicted in FIGS. 17-19. Each of these springs, as depicted, includes a combination of an electrically conductive material and an electrically insulative material. The electrically conductive material is depicted in the dark shading and the electrically insulative material is depicted in the lighter shading. However, in some embodiments the electrically insulative material can be omitted.

The spring 400 shown in FIG. 17 includes multiple spring segments that are each C-shaped. Contact portions are located on the opposing ends of each of the C-shaped spring segments. The resistance of the spring segments reduce when the contact portions of the spring segments come into contact with each other (in the same manner as described above in the context of the spring 200). The spring 400 is well suited for use along a curved axis, among other uses.

The spring 500 shown in FIG. 18 includes traces of the conductive material along the entirety of each of the arms of the multiple spring segments (as opposed to the spring 200 that includes traces of the conductive material along a half of each of the arms of the multiple spring segments).

The spring 600 shown in FIG. 19 includes traces of the conductive material along a half of each of the arms of the multiple spring segments (which the spring 200 also includes). However, the construction of the spring 600 differs from the construction of the spring 200 in that the traces of the conductive material of the spring 600 extend along alternating side arms of the spring segments, whereas the traces of the conductive material of the spring 600 extend along the same side arms of the spring segments.

It should be understood that the features and variations of the springs 200, 300, 400, 500, and 600 can be combined in any desired manner. All combinations and permutations of such embodiments are within the scope of this disclosure.

The springs described herein that can provide electrical signals/outputs that are indicative of the deformation of the spring have a number of practical uses. One example use for such springs is in the context of a 3D printed shoe midsole.

Figure 20:
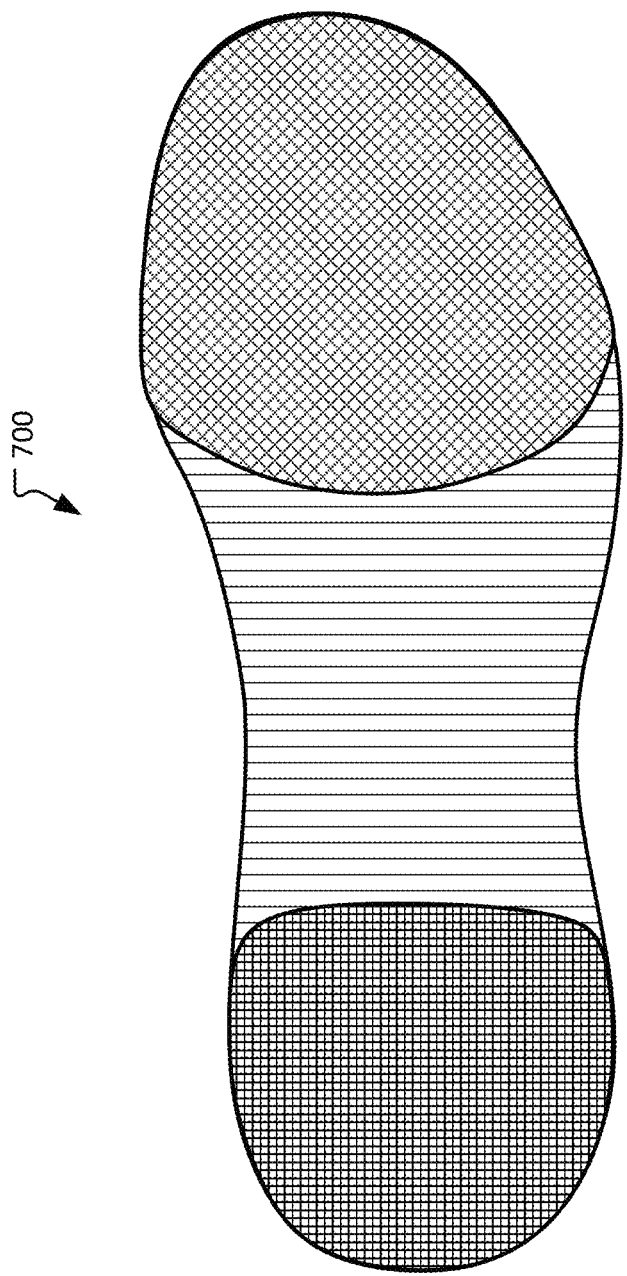
FIG. 20 illustrates an example shoe midsole that can utilize concepts of the springs described herein.

FIG. 20 illustrates an example 3D printed shoe midsole 700. This midsole 700 has a 3D printed lattice structure where the density of the lattice is varied in different functional zones to tune the energy return properties in specific areas of the shoe. Traditional midsoles are made from compression molded EVA foam, polyurethane or TPU. Instead, this midsole 700 is 3D printed (including multi-material 3D printed in some embodiments).

Using the techniques for the springs described above, the midsole 700 can include a very thin embedded pressure sensitive layer to measure where various levels of force are being applied, and to give feedback to the user.

By instrumenting the elastic 3D-printed midsole 700 with a conductive material to create the types of springs described above at one or more locations of the midsole 700, pressure distributions can be recorded from the runner's stride through the springs themselves without the need of an external sensor that adds weight. Using this information, the timing of the energy release can be optimized for greater energy return and may lead to more accurate step count measurement and activity classification.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results.

What is claimed is:

1. A spring comprising:
   a first 3D printed material;
   a second 3D printed material integrated with the first 3D printed material and having an electrical conductivity that is greater than an electrical conductivity of the first 3D printed material;
   a first electrical contact connected to the second 3D printed material; and
   a second electrical contact connected to the second 3D printed material,
   wherein the spring is configured to have an electrical conductivity between the first and second electrical contacts that changes in response to deformation of the spring, and
   wherein the second 3D printed material between the first and second electrical contacts is at least partially encapsulated within the first 3D printed material.

2. The spring of claim 1, wherein the deformation of the spring deforms each of the first and second 3D printed materials.

3. The spring of claim 1, wherein the spring is a coil spring.

4. The spring of claim 1, wherein the spring is a cantilever spring.

5. The spring of claim 1, wherein the changes of the electrical conductivity in response to the deformation of the spring are proportional to the deformation of the spring.

6. The spring of claim 1, wherein the changes of the electrical conductivity in response to the deformation of the spring include a one or more step changes.

7. The spring of claim 1, wherein the second 3D printed material between the first and second electrical contacts comprises a portion of an outer surface of the spring.

8. The spring of claim 1, wherein the second 3D printed material between the first and second electrical contacts is entirely encapsulated within the first 3D printed material.

9. The spring of claim 1, wherein only the second 3D printed material is between the first and second electrical contacts.

10. A method of making a spring, the method comprising using a multi-material 3D printing process to form a first material and a second material into a spring shape,
   wherein, at multiple cross-sections of the spring, the second material is entirely encapsulated within the first material,
   wherein the second material has an electrical conductivity that is greater than an electrical conductivity of the first material, and
   wherein elastic deformations of the spring are detectable by measuring the electrical conductivity of the second material.

11. The method of claim 10, wherein the multi-material 3D printing process is a dual extrusion process, and
   wherein, during at least some portions of the forming, the first and second materials are deposited concurrently.

12. The method of claim 11, wherein, at multiple cross-sections of the spring, the first material comprises a first portion of an outer periphery of the spring and the second material comprises a second portion of the outer periphery of the spring.

13. The method of claim 10, wherein the spring includes only the second material at multiple cross-sections of the spring.

14. The method of claim 10, wherein the spring shape is a coil spring.

15. The method of claim 10, wherein the spring shape is a cantilevered spring.

16. A coil spring comprising:
   a 3D printed material having an electrical conductivity and an infill density percentage of less than 100%;
   a first electrical contact connected to the 3D printed material; and
   a second electrical contact connected to the 3D printed material,
   wherein the coil spring is configured to have an electrical conductivity between the first and second electrical contacts that changes in response to deformation of the coil spring.

17. A spring comprising:
   a first spring segment having a first spring constant, an uncompressed configuration, a partially compressed configuration, and a fully compressed configuration; and
   a second spring segment having a second spring constant, an uncompressed configuration, a partially compressed configuration, and a fully compressed configuration,
   wherein the second spring constant is greater than the first spring constant,
   wherein the first and second spring segments are arranged in series,
   wherein a first electrical circuit between a first electrical contact on the first spring segment and a second electrical contact on the second spring segment has a first resistivity when: (i) the first spring segment is in the uncompressed configuration, and (ii) the first spring segment is in the partially compressed configuration, and wherein the first electrical circuit has a second resistivity when the first spring segment is in the fully compressed configuration, and
   wherein the first resistivity is greater than the second resistivity.

18. The spring of claim 17, wherein the first electrical circuit has a third resistivity when the first spring segment is in the fully compressed configuration and the second spring segment is in the fully compressed configuration, and wherein the third resistivity is less than the second resistivity.

19. The spring of claim 17, wherein the spring is a multi-material 3D printed spring.

* * * * *